United States Patent
Linder et al.

(10) Patent No.: US 9,221,761 B2
(45) Date of Patent: Dec. 29, 2015

(54) METHOD FOR INHIBITION OF DEUBIQUITINATING ACTIVITY

(71) Applicant: Vivolux AB, Uppsala (SE)

(72) Inventors: Stig Linder, Bromma (SE); Rolf Larsson, Uppsala (SE)

(73) Assignee: Vivolux AB, Uppsala (SE)

( * ) Notice: Subject to any disclaimer, the term of this patent is extended or adjusted under 35 U.S.C. 154(b) by 0 days.

(21) Appl. No.: 14/256,280

(22) Filed: Apr. 18, 2014

(65) Prior Publication Data

US 2014/0228354 A1 Aug. 14, 2014

Related U.S. Application Data

(63) Continuation of application No. PCT/SE2012/000158, filed on Oct. 15, 2012.

(30) Foreign Application Priority Data

| Oct. 19, 2011 | (SE) | ................................... 1100776 |
| May 16, 2012 | (SE) | ................................... 1200303 |

(51) Int. Cl.

| *A61K 31/55* | (2006.01) |
| *C07D 223/00* | (2006.01) |
| *C07D 223/08* | (2006.01) |
| *C07D 401/06* | (2006.01) |
| *C07D 403/06* | (2006.01) |
| *C07D 409/06* | (2006.01) |
| *A61K 9/28* | (2006.01) |

(52) U.S. Cl.

CPC ................ *C07D 223/08* (2013.01); *A61K 9/28* (2013.01); *A61K 31/55* (2013.01); *C07D 401/06* (2013.01); *C07D 403/06* (2013.01); *C07D 409/06* (2013.01)

(58) Field of Classification Search
CPC .............................. C07D 223/08; A61K 31/55
See application file for complete search history.

(56) References Cited

FOREIGN PATENT DOCUMENTS

| WO | 2007/007207 A2 | 1/2007 |
| WO | 2007/059613 A1 | 5/2007 |
| WO | 2011/005790 A1 | 1/2011 |
| WO | WO2013058691 A1 * | 4/2013 |

OTHER PUBLICATIONS

Sacco, J., et al. "Emerging Roles of Deubiquitinases in Cancer-Associated Pathways." IUBMB Life. (Feb. 2010), vol. 62, 2, pp. 140-157.*
National Cancer Institute. "Cancer Drug Information." © 2014. Available from: < http://www.cancer.gov/cancertopics/druginfo/alphalist/print >.*
National Cancer Institute. "Drugs Approved for Different Types of Cancers." (c) 2014. Available from: < http://www.cancer.gov/cancertopics/druginfo/drug-page-index/print >.*
Romagnoli et al, Bioorg. Med. Chem. Lett., 20:2733-2739 (2010).
Berndtsson et al, Int. J. Cancer, 124:1463-1469 (2009).
Aleo et al, Cancer Res., 66(18):9235-9244 (2006).
D'Arcy et al, Nature Medicine, 17(12):1636-1641, Dec. 2011, Online Nov. 6, 2011, and Supplementary Text, pp. 1-17).

* cited by examiner

*Primary Examiner* — Noble Jarrell
*Assistant Examiner* — John S Kenyon
(74) *Attorney, Agent, or Firm* — Porter Wright Morris & Arthur LLP

(57) ABSTRACT

Compounds of the general structure S-1, wherein X and $R^1$-$R^5$ are defined in the specification, are capable of abrogating the deubiquitinating (DUB) activity of the 19S RP DUBs and are useful in methods and compositions for treating cancer, in particular, cancer tumors refractory to treatment by state-of-the-art chemotherapy.

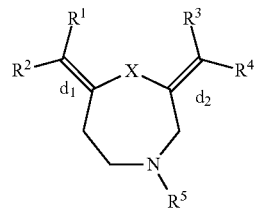

S-1

30 Claims, 13 Drawing Sheets

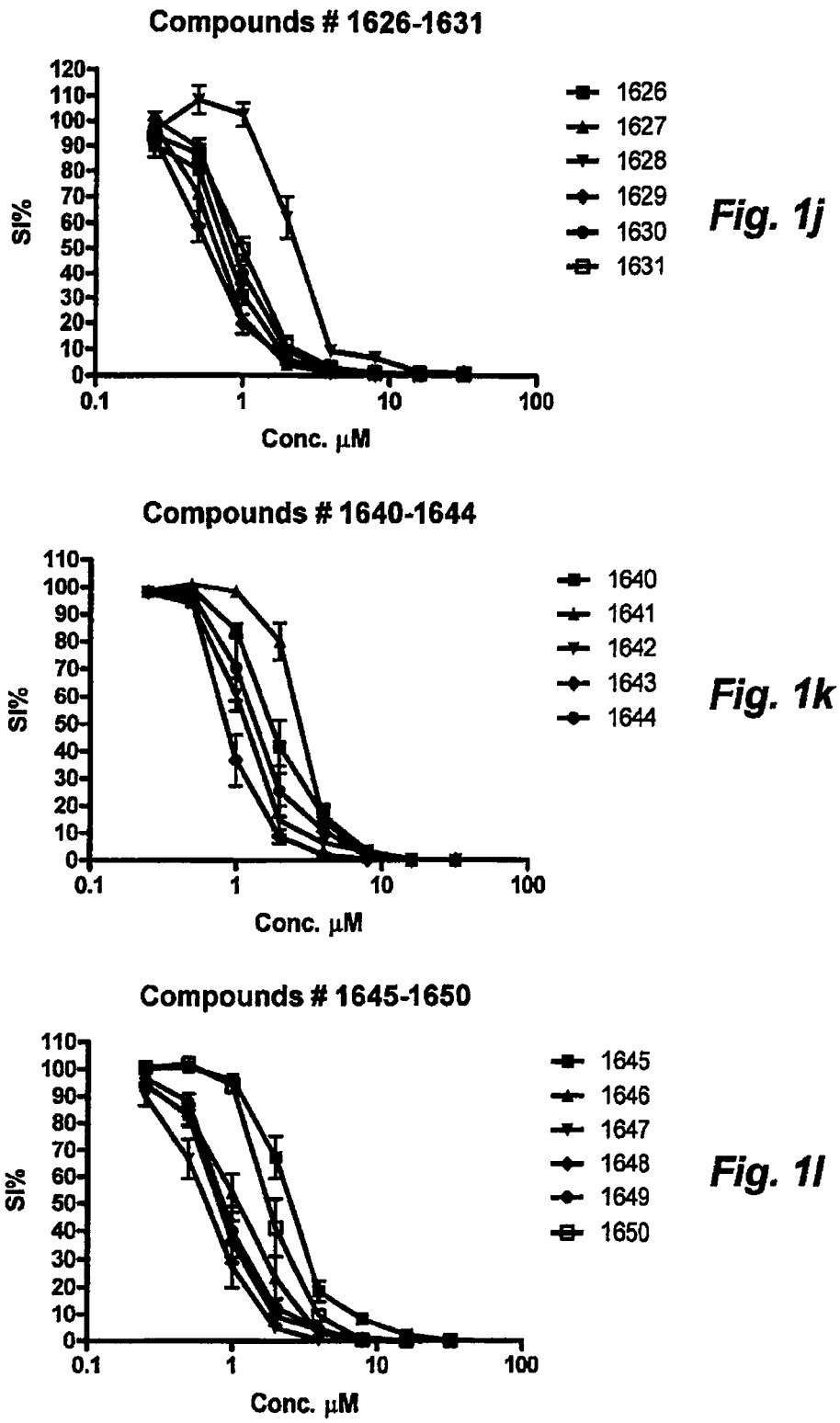

METHOD FOR INHIBITION OF DEUBIQUITINATING ACTIVITY

FIELD OF THE INVENTION

The invention relates to a method of treating cancer in a patient by inhibiting deubiquitinating activity. More particularly, the invention relates to a method of treating a cancer in a patient who has proved resistant to treatment by at least one anti-cancer medicine. Most particularly, the invention relates to a compound for use in the method and to a pharmaceutical composition comprising the compound.

BACKGROUND OF THE INVENTION

Tumor cells display enhanced sensitivity to disruptions in the ubiquitin-proteasome system (UPS) making this an attractive target for the development of anti-cancer therapies (1). Ubiquitin-tagged substrates are degraded by the 26S proteasome, a multi-subunit complex comprising a proteolytic 20S core (20S CP) capped by 19S regulatory particles (19S RP) (2,3). The 20S CP has evolved as an important target for anti-cancer drug development, resulting in the approval of bortezomib (Velcade®) for treatment of myeloic leukemia (4).

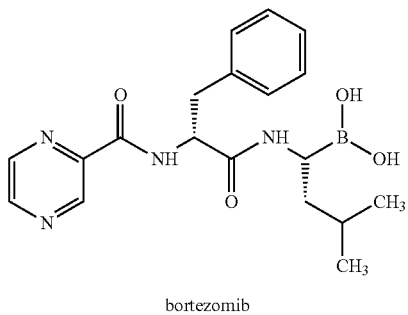

bortezomib

The compound b-AP15 (NSC687852) is known to induce p53-independent and cathepsin-D-dependent apoptosis (5,6).

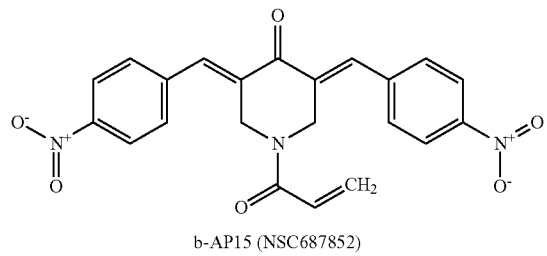 [SMILES: C=CC(=O)N1C/C(=C\c2ccc([N+](=O)[O-])cc2)C(=O)/C(=C/c2ccc([N+](=O)[O-])cc2)C1]

b-AP15 (NSC687852)

OBJECTS OF THE INVENTION

It is an object of the invention to provide a compound for use in a method of treating cancer in a patient by inhibiting deubiquitinating activity, in particular a cancer refractory to state-of-the-art chemotherapy.

In particular, it is an object of the invention to provide such a compound for treating cancer in a patient refractory to treatment with at least bortezomib or an agent sharing the mechanism of deubiquitinating activity inhibition of bortezomib.

Another object of the invention is to provide a compound of the aforementioned kind, which has improved solubility at physiological ph in respect of functionally equivalent compounds known in the art.

An additional object of the invention is to provide a corresponding method.

A further object of the invention is to provide a pharmaceutical composition comprising the compound.

Still further objects of the invention will become evident by studying the following summary of the invention, a number of preferred embodiments thereof illustrated in a drawing, and the appended claims.

SUMMARY OF THE INVENTION

According to the present invention is disclosed a compound of the general structure S:

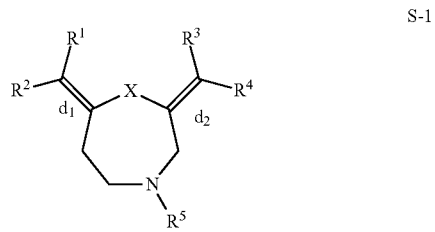

S-1 capable of abrogating the deubiquitinating (DUB) activity of the 19S RP DUBs.

The compound of the invention is recognized as pertaining to a novel class of proteasome inhibitors of which the known compound b-AP15 is a representative.

In particular, according to the present invention, the compound of the invention inhibits the activity of two 19S RP DUBs, UCHL5 and USP14 while not affecting non-proteasomal DUBs. More particularly, the compound of the invention has effect in the treatment of a cancer tumor refractory to state-of-the-art chemotherapy due to over-expression of the intrinsic apoptosis-inhibitor Bcl-2.

Most particularly, according to the present invention, the compound of the invention is effective in the treatment of a cancer refractory to treatment with bortezomib or an agent sharing the mechanism of deubiquitinating inhibition of bortezomib. In another preferred embodiment, the compound is effective in the treatment of a cancer refractory to any anti-cancer drug known in the art.

In this application, "refractory to treatment" signifies that treatment of a cancer with a single dose of an anti-cancer medicine does not substantially reduce the growth rate of the cancer observed immediately prior to the treatment, such as reducing the growth rate per month by not more than 25 percent or 10 percent or even 5 percent or less. In particular, the method of the invention is efficient in treating a cancer in a patient which, after having received one or more, in particular two or three, standard doses of bortezomib or an agent sharing the apoptosis generating activity of bortezomib or any other anti-cancer drug, exhibits a cancer growth rate per month reduced by not more than 25 percent or 10 percent or even 5 percent or less, such as any positive growth rate, in comparison with the cancer growth rate observed immediately prior to the single treatment or to the last of two or three or more treatments, respectively. An accepted measure of tumor growth is the change of volume of a non-disseminated cancer.

An example of a cancer amenable to treatment by the method of the invention is multiple myeloma. Other examples of cancers amenable to treatment comprise lung cancer, prostate cancer, colon cancer, ovary cancer, pancreas cancer, breast cancer, neck & head cancer.

In the compound of the invention of the general structure S-1, $R^1$, $R^2$ at double bond d1 and $R^3$, $R^4$ at double bond d2 can, independent of each other, have a configuration opposite to that of formula S-1, X is CO, CS, $CH_2$, $CHC_{1-6}$-alkyl, NH or $NC_{1-6}$-alkyl;

$R^1$ and $R^3$ are, independent of each other, H or $C_{1-6}$-alkyl;

$R^2$ and $R^4$ are, independent of each other, H; $C_{1-6}$-alkyl; $C_{1-5}$-alkylCO; phenyl or 6-membered heteroaryl optionally substituted by 1-3 of: $C_{1-6}$-alkyl, $C_{1-6}$-alkoxy, CN, —$COOC_{1-6}$ alkyl, COOH, $NO_2$, F, Cl, Br, I, $CF_3$, $NH_2$, $NHC_{1-6}$-alkyl, $N(C_{1-6}$-alkyl$)_2$, $CONR^7R^8$, with the proviso that one or more of H in alkyl and alkoxy can be substituted by fluoro;

$R^5$ is H; $C_{1-6}$-alkyl; $C_{2-6}$-alkenyl; $C_{1-3}$-alkoxy-$C_{1-6}$-alkyl-; $C_{1-3}$-alkoxy-$C_{2-6}$-alkenyl-; aryl-$C_{0-6}$-alkyl-; heteroaryl-$C_{0-6}$-alkyl-; heterocyclyl-$C_{0-6}$-alkyl-; cycloalkyl-$C_{0-6}$-alkyl-; —$C_{1-6}$-alkyl-$COOC_{1-6}$-alkyl; —$C_{2-6}$-alkyl-aryloxy; $C_{1-6}$-alkyl-heteroaryl; $C_{1-6}$-alkyl-heterocyclyl; $C_{1-6}$-alkyl-cycloalkyl; $C_{1-6}$-alkyl-aryl; $COR^6$;

$R^6$ is selected from: $C_{1-6}$-alkyl; $C_{2-6}$-alkenyl; $C_{1-6}$-alkoxy; $C_{1-3}$-alkoxy-$C_{1-6}$-alkyl-; $C_{1-3}$-alkoxy-$C_{2-6}$-alkenyl-; aryl-$C_{0-6}$-alkyl-; heteroaryl-$C_{0-6}$-alkyl-; heterocyclyl-$C_{0-6}$-alkyl-; cycloalkyl-$C_{0-6}$-alkyl-; —$C_{1-6}$-alkyl-$COOC_{1-6}$-alkyl; $NH_2$; —$NHC_{1-6}$-alkyl; —$N(C_{1-6}$-alkyl$)_2$; —$C_{0-6}$-alkyl-aryloxy;

$R^7$, $R^8$ are, independent of each other, H or $C_{1-3}$-alkyl.

It is preferred for both of $R^1$ and $R^3$ to be or $C_{1-3}$-alkyl.

It is preferred for both of $R^2$ and $R^4$ to be H; $C_{1-6}$-alkyl; $C_{1-5}$-alkylCO; phenyl or 6-membered heteroaryl optionally substituted by 1-3 of: $C_{1-6}$-alkyl, $C_{1-6}$-alkoxy, CN, $COOC_{1-6}$-alkyl, COOH, $NO_2$, F, Cl, Br, I, $CF_3$, $NH_2$, $NHC_{1-6}$-alkyl, $N(C_{1-6}$-alkyl$)_2$, $CONR^7R^8$, with the proviso that one or more of H in alkyl and alkoxy can be substituted by fluoro, and wherein substitution of phenyl is preferably at one or more of positions 3, 4, 5.

It is particularly preferred for both of $R^2$ and $R^4$ to be phenyl substituted at one or more of positions 3, 4, 5 by 1-3, preferably by 1 or 2, of: $C_{1-6}$-alkyl, $C_{1-6}$-alkoxy, CN, —$COOC_{1-6}$ alkyl, COOH, $NO_2$, F, Cl, Br, I, $CF_3$, $NH_2$, $NHC_{1-6}$-alkyl, $N(C_{1-6}$-alkyl$)_2$, $CONR^7R^8$, with the proviso that one or more of H in alkyl and alkoxy can be substituted by fluoro. Most preferred are electron-withdrawing substituents, in particular F, Cl, trifluoromethyl, $NO_2$, CN.

It is preferred for $R^5$ to be selected from the group consisting of H, methyl, acetyl, $COCH=CH_2$, 2-acetoxyethyl.

According to a preferred aspect of the invention X=CO. According to another preferred aspect of the invention $R^1$ and $R^3$ are both H. According to a third preferred aspect of the invention, $R^2$ and $R^4$ are, independent of each other, phenyl or 6-membered heteroaryl optionally substituted by 1-3 of: $C_{1-6}$-alkyl, $C_{1-6}$-alkoxy, CN, —$COOC_{1-6}$-alkyl, COOH, $NO_2$, F, Cl, Br, I, $CF_3$, $NH_2$, $NHC_{1-6}$-alkyl, $N(C_{1-6}$-alkyl$)_2$, $CONR^2R^8$, phenyl being preferred and substitution of phenyl, if any, being preferred in one or more of positions 3, 4, 5.

According to a preferred aspect of the invention $R^1$, $R^2$ at double bond d1 and $R^3$, $R^4$ at double bond d2 have the configuration of formula S-1; X is CO, CS, $CH_2$, $CHC_{1-6}$-alkyl, NH or $NC_{1-6}$-alkyl; $R^1$ and $R^3$ are, independent of each other, H or $C_{1-6}$-alkyl; $R^2$ and $R^4$ are, independent of each other, H; $C_{1-6}$-alkyl; $C_{1-5}$-alkylCO; phenyl or 6-membered heteroaryl substituted with 1-3 of: CN, $NO_2$, F, Cl, Br, I, $NH_2$, $NHC_{1-6}$-alkyl, $N(C_{1-6}$-alkyl$)_2$, $COC_{1-6}$-alkyl; $R^5$ is H, $C_{1-6}$-alkyl, $C_{2-6}$-alkenyl, $C_{1-3}$-alkoxy-$C_{1-6}$-alkyl, $C_{1-3}$-alkoxy-$C_{2-6}$-alkenyl, aryl, heteroaryl, heterocyclyl, $C_{1-6}$-alkyl-heteroaryl, $C_{1-6}$-alkyl-heterocyclyl, $C_{1-6}$-alkyl-cycloalkyl, $C_{1-6}$-alkyl-aryl, CO—$C_{1-6}$-alkyl, CO-vinyl, CO-allyl, CO-aryl, CO-cycloalkyl. It is preferred, independent of each other, for X to be CO, for $R^2$ and $R^4$ to be substituted phenyl, for $R^5$ to be selected from $COR^6$, in particular from CO—$C_{1-6}$-alkyl, CO-cycloalkyl, CO-vinyl, CO-allyl.

"Aryl" refers to a monocyclic or bicyclic hydrocarbon of from 6 to 10 carbon atoms comprising at least one aromatic ring. "Aryloxy" refers to an aryl group bonded to an oxygen atom. "Heteroaryl" represents a monocyclic ring system having 5 or 6 ring atoms, of which one or more are selected independently from oxygen, nitrogen, sulphur. "Alkyl" denotes straight or branched alkyl. "Alkenyl" denotes straight or branched alkenyl. "Alkoxy" denotes straight or branched alkoxy. "Cycloalkyl" refers to a saturated monocyclic hydrocarbon of from 3 to 7 carbon atoms.

Preferred compounds of the invention of the general structure S-1 are disclosed in Tables 1 and 2.

TABLE 1

Preferred compounds of the invention
X = CO, $R^1$ = $R^3$ = H, $R^5$ is H or alkyl

| # | $R^2$ | $R^4$ | $R^5$ | HCT116, FMCA, IC50 (µM) | MeJuSo-UB, IncuCyte lowest effective conc. (µM) |
|---|---|---|---|---|---|
| 1516 | phenyl | phenyl | H | | 1.2 |
| 1517 | 4-methoxyphenyl | 4-methoxyphenyl | H | | |
| 1518 | 4-chlorphenyl | 4-chlorophenyl | H | | 1.6 |
| 1533 | 3-acetylphenyl | 3-acetylphenyl | H | | |
| 1535 | 3-nitrophenyl | 3-nitrophenyl | H | 5.9 | |
| 1536 | 2-nitrophenyl | 2-nitrophenyl | H | 6.9 | |
| 1537 | 4-nitrophenyl | 4-nitrophenyl | H | 4.1 | |
| 1560 | 4-nitrophenyl* | H** | H | 1.0 | |
| 1561 | 4-fluorophenyl | 4-fluorophenyl | H | 1.0 | 1 |
| 1562 | 4-fluoro-3-nitrophenyl | 4-fluoro-3-nitrophenyl | H | 0.5 | 0.25 |
| 1563 | 4-nitrophenyl | 4-nitrophenyl | methyl | 1.5 | 0.5 |
| 1564 | 4-fluorophenyl | 4-fluorophenyl | methyl | 0.9 | 16 |
| 1565 | 4-fluoro-3-nitrophenyl | 4-fluoro-3-nitrophenyl | methyl | 1.5 | 0.5 |
| 1566 | 3-nitrophenyl | 3-nitrophenyl | methyl | 2.3 | 0.5 |
| 1574 | 4-fluorophenyl | 4-fluorophenyl | propyl | 2.8 | 0.5 |
| 1575 | 4-nitrophenyl | 4-methoxyphenyl | H | 2.1 | 1 |
| 1576 | 4-fluorophenyl | 4-methoxyphenyl | H | 1.6 | 8 |
| 1577 | 4-fluorophenyl | 4-methoxyphenyl | methyl | 4.9 | 8 |
| 1582 | 4-fluorophenyl | 4-chlorophenyl | H | 1.7 | 2 |
| 1583 | 4-chlorophenyl | 4-nitrophenyl | methyl | 3.3 | 2 |

TABLE 1-continued

Preferred compounds of the invention
X = CO, $R^1 = R^3 = H$, $R^5$ is H or alkyl

| # | $R^2$ | $R^4$ | $R^5$ | HCT116, FMCA, IC50 (µM) | MeJuSo-UB, IncuCyte lowest effective conc. (µM) |
|---|---|---|---|---|---|
| 1584 | 4-chlorophenyl | 4-nitrophenyl | H | 1.8 | 2 |
| 1585 | 4-fluorophenyl | 4-nitrophenyl | H | 1.5 | 2 |
| 1586 | 4-chlorophenyl | 4-fluorophenyl | H | 1.1 | 0.5 |
| 1587 | 4-fluorophenyl | 4-nitrophenyl | methyl | 3.0 | 1 |
| 1588 | 4-nitrophenyl | 4-methoxyphenyl | methyl | 3.1 | 1 |
| 1589 | 4-chlorophenyl | 4-fluorophenyl | methyl | 2.5 | 1 |
| 1590 | 4-chlorophenyl | 4-methoxyphenyl | methyl | 2.0 | 1 |
| 1591 | 4-nitrophenyl | 4-chlorophenyl | H | 0.9 | 0.5 |
| 1592 | 4-chlorophenyl | 4-nitrophenyl | H | 12 | 4 |
| 1593 | 4-nitrophenyl | 4-fluorophenyl | methyl | 2.9 | 1 |
| 1594 | 4-nitrophenyl | 4-chlorophenyl | methyl | 2.6 | 1 |
| 1595 | 4-fluorophenyl | 4-chlorophenyl | methyl | 2.3 | 1 |
| 1596 | 4-nitrophenyl | 4-fluorophenyl | H | 2.6 | 2 |
| 1608 | 3-chloro-4-fluoro-phenyl | 3-chloro-4-fluoro-phenyl | methyl | 1.8 | 1 |
| 1609 | 4-fluoro-3-trifluoro-methyl-phenyl | 4-fluoro-3-trifluoro-methyl-phenyl | methyl | 1.4 | 1 |
| 1610 | 3,4-difluorophenyl | 3,4-difluorophenyl | methyl | 1.7 | 1 |
| 1611 | 3-fluoro-5-trifluoro-methyl-phenyl | 3-fluoro-5-trifluoro-methyl-phenyl | H | 1.1 | 0.5 |
| 1612 | 3-fluoro-5-trifluoro-methyl-phenyl | 3-fluoro-5-trifluoro-methyl-phenyl | methyl | 0.7 | 0.25 |
| 1613 | 4-nitrophenyl | 4-nitrophenyl | H | 25 | 32 |
| 1614 | 4-nitrophenyl | 4-nitrophenyl | methyl | 7.4 | 8 |
| 1615 | 4-chloro-3-trifluoro-methylphenyl | 4-chloro-3-trifluoro-methylphenyl | methyl | 0.9 | 0.5 |
| 1616 | 3,4,5-trifluoromethyl-phenyl | 3,4,5-trifluoromethyl-phenyl | methyl | 1.4 | 0.5 |
| 1617 | 4-trifluoromethyl-phenyl | 4-trifluorometyl-phenyl | methyl | 1.6 | 1 |
| 1618 | 3-cyano-4-fluoro-phenyl | 3-cyano-4-fluoro-phenyl | methyl | 1.5 | 0.5 |
| 1619 | 3-carbonylamino-phenyl | 3-carbonylamino-phenyl | H | 30 | 32 |
| 1620 | 3-nitrophenyl | 3-nitrophenyl | methyl | >32 | no effect |
| 1621 | 4-cyanophenyl | 4-cyanophenyl | methyl | 4.5 | 2 |
| 1622 | 4-fluoro-3-trifluoro-methyl-phenyl | 4-fluoro-3-trifluoro-methyl-phenyl | H | 0.8 | 0.5 |
| 1623 | 3-cyano-4-fluoro-phenyl | 3-cyano-4-fluoro-phenyl | H | 1.0 | 0.5 |
| 1624 | 3-fluoro-4-trifluoro-methyl-phenyl | 3-fluoro-4-trifluoro-methyl-phenyl | methyl | 1.8 | 1 |
| 1625 | 4-cyanophenyl | 4-cyanophenyl | H | 0.9 | 0.5 |
| 1626 | 3-fluoro-4-trifluoro-methyl-phenyl | 3-fluoro-4-trifluoro-methyl-phenyl | H | 0.8 | 8 |

*or H or a mixture of H and 4-nitrophenyl
**or 4-nitrophenyl or a mixture of H and 4-nitrophenyl Due to protonation of their amino group the solubility in aqueous media of azepanone compounds of the invention of which $R^5$ is not acyl as well as of correspondingly substituted piperidin-4-ones increases with decreasing pH. However, according to an important aspect azepanone compounds of the invention of which $R^5$ is not acyl (that is, not —$COR^6$) have superior solubility in aqueous media at physiological pH in comparison with correspondingly substituted piperidin-4-ones. While the solubility of these azepanones and piperidine-4-ones increases in going from a high pH to a low pH, the increase starts at higher pH values for the azepanones than for the corresponding piperidin-4-ones. In this application "physiological pH" is a pH of from about 6 to about 8, in particular from 7.0 to 7.5.

TABLE 2

Preferred compounds of the invention
X = CO, $R^1 = R^3 = H$, $R^5 = COR^6$

| # | $R^2$ | $R^4$ | $R^6$ | HCT116, FMCA, IC50 (µM) | MeJuSo-UB, lowest effective conc. (µM) |
|---|---|---|---|---|---|
| 1505 | 4-nitrophenyl | 4-nitrophenyl | 2-pyrrolidinyl | 5.2 | 16 |
| 1507 | 4-nitrophenyl | 4-nitrophenyl | 2-(1-carboxyethyl-ethyl) | 4.4 | 8 |

TABLE 2-continued

Preferred compounds of the invention
X = CO, R$^1$ = R$^3$ = H, R$^5$ = COR$^6$

| # | R$^2$ | R$^4$ | R$^6$ | HCT116, FMCA, IC50 (μM) | MeJuSo-UB, lowest effective conc. (μM) |
|---|---|---|---|---|---|
| 1520 | phenyl | phenyl | vinyl | | |
| 1521 | phenyl | phenyl | cyclobutyl | | |
| 1525 | 4-methoxyphenyl | 4-methoxyphenyl | cyclobutyl | | |
| 1526 | 4-methoxyphenyl | 4-methoxyphenyl | cyclopropyl | | |
| 1527 | 4-chlorophenyl | 4-chlorophenyl | cyclobutyl | | 2 |
| 1546 | 4-nitrophenyl | 4-nitrophenyl | vinyl | 1.2 | 2 |
| 1567 | 4-nitrophenyl | 4-nitrophenyl | methyl | 0.6 | 0.5 |
| 1568 | 4-fluorophenyl | 4-fluorophenyl | vinyl | 1.5 | 2 |
| 1569 | 4-fluorophenyl | 4-fluorophenyl | vinyl | 2.0 | 4 |
| 1570 | 4-fluoro-3-nitrophenyl | 4-fluoro-3-nitrophenyl | vinyl | 0.5 | 0.25 |
| 1571 | 4-fluoro-3-nitrophenyl | 4-fluoro-3-nitrophenyl | methyl | 0.9 | 0.25 |
| 1572 | 3-nitrophenyl | 3-nitrophenyl | vinyl | 2.5 | 0.5 |
| 1578 | 4-fluorophenyl | 4-methoxyphenyl | methyl | 7.0 | 8 |
| 1579 | 4-fluorophenyl | 4-methoxyphenyl | methyl | 5.9 | 8 |
| 1580 | 4-nitrophenyl | 4-methoxyphenyl | vinyl | 1.5 | 8 |
| 1581 | 4-nitrophenyl | 4-methoxyphenyl | methyl | 7.2 | 8 |
| 1597 | 4-nitrophenyl | 4-chlorophenyl | methyl | 1.3 | 1 |
| 1627 | 4-trifluoromethyl-phenyl | 4-trifluoromethyl-phenyl | methyl | 0.7 | 1 |
| 1628 | 3,4-difluorophenyl | 3,4-difluorophyenyl | methyl | 2.3 | 1 |
| 1629 | 3,4,5-trifluorophenyl | 3,4,5-trifluorophenyl | methyl | 0.6 | 1 |
| 1630 | 4-chloro-3-fluoro-phenyl | 4-chloro-3-fluoro-phenyl | methyl | 0.9 | 0.5 |
| 1631 | 3-chloro-4-fluoro-phenyl | 3-chloro-4-fluoro-phenyl | methyl | 1.0 | 32 |
| 1633 | 4-chlorophenyl | 4-chlorophenyl | 2-acetoxyethyl | 2.2 | 4 |
| 1635 | 4-chlorophenyl | 4-chlorophenyl | benzyl | 1.4 | 2 |
| 1636 | 4-chlorophenyl | 4-chlorophenyl | 1-(3-phenyl-2-propenyl) | 2.0 | 1 |
| 1637 | 4-chlorophenyl | 4-chlorophenyl | 3-pyridyl | 2.1 | 2 |
| 1638 | 4-chlorophenyl | 4-chlorophenyl | 2-thiophenyl | 2.0 | 2 |
| 1639 | 4-chlorophenyl | 4-chlorophenyl | 4-hydroxy-3-ethoxybenzyl | 1.2 | 1 |
| 1640 | 4-chlorophenyl | 4-chlorophenyl | methyl-(2-methoxy-carboxyl)phenyl | 1.9 | 1 |
| 1641 | 4-trifluoromethyl-phenyl | 4-trifluoromethyl-phenyl | methyl-3-pyridyl | 2.7 | 2 |
| 1642 | 4-trifluoromethyl-phenyl | 4-trifluoromethyl-phenyl | 2-oxo-acetoxyethyl | 1.2 | 1 |
| 1643 | 4-trifluoromethyl-phenyl | 4-trifluoromethyl-phenyl | 3-(3-oxo-propanoyloxy-methyl) | 0.9 | 1 |
| 1644 | 4-trifluoromethyl-phenyl | 4-trifluoromethyl-phenyl | 1-oxo-2-(2-pyridyl)ethyl | 1.4 | 1 |
| 1645 | 4-chloro-3-fluoro-phenyl | 4-chloro-3-fluoro-phenyl | 2-oxo-acetoxyethyl | 2.5 | 2 |
| 1646 | 4-fluoro-3-nitro-phenyl | 4-fluoro-3-nitro-phenyl | 2-oxo-acetoxymethyl | 1.1 | 1 |
| 1647 | 4-fluoro-3-nitro-phenyl | 4-fluoro-3-nitro-phenyl | 3-(3-oxo-propanoyloxy-methyl) | 0.7 | 0.25 |
| 1648 | 4-fluoro-3-nitro-phenyl | 4-fluoro-3-nitro-phenyl | 1-oxo-2-(2-pyridyl)ethyl | 0.8 | 0.5 |
| 1649 | 3,4,5-trifluoro-phenyl | 3,4,5-trifluoro-phenyl | methyl-(2-methoxy-carboxyl)phenyl | 0.9 | 0.5 |
| 1650 | 3,4,5-trifluoro-phenyl | 3,4,5-trifluoro-phenyl | methyl-3-pyridyl | 1.9 | 1 |
| 1651 | 3,4,5-trifluoro-phenyl | 3,4,5-trifluoro-phenyl | 2-oxo-acetoxyethyl | 0.8 | 0.5 |
| 1652 | 3,4,5-trifluoro-phenyl | 3,4,5-trifluoro-phenyl | 3-(3-oxo-propanoyloxy-methyl | 0.6 | 0.5 |
| 1653 | 3,4,5-trifluoro-phenyl | 3,4,5-trifluoro-phenyl | 1-oxo-2-(2-pyridyl)ethyl | 0.71 | 1 |
| 1654 | 4-chloro-3-trifluoro methyl-phenyl | 4-chloro-3-fluoro-methyl-phenyl | methyl-(2-methoxy-carboxyl)phenyl | 1.2 | 1 |
| 1655 | 4-chloro-3-trifluoro methyl-phenyl | 4-chloro-3-trifluoro methyl-phenyl | methyl-3-pyridyl | 1.0 | 1 |
| 1656 | 4-chloro-3-trifluoro methyl-phenyl | 4-chloro-3-trifluoro methyl-phenyl | 2-oxo-acetoxyethyl | 0.7 | 0.5 |
| 1657 | 4-chloro-3-trifluoro methyl-phenyl | 4-chloro-3-trifluoro methyl-phenyl | acetyl | 0.6 | 0.5 |

TABLE 2-continued

Preferred compounds of the invention
X = CO, $R^1 = R^3 = H$, $R^5 = COR^6$

| # | $R^2$ | $R^4$ | $R^6$ | HCT116, FMCA, IC50 (μM) | MeJuSo-UB, lowest effective conc. (μM) |
|---|---|---|---|---|---|
| 1658 | 4-chloro-3-trifluoro methyl-phenyl | 4-chloro-3-trifluoro methyl-phenyl | 1-oxo-2-(2-pyridyl)ethyl | 0.8 | 0.5 |
| 1659 | 4-trifluoromethyl-phenyl | 4-trifluoromethyl-phenyl | 2-acetoxyethyl | 2.4 | 2 |
| 1660 | 4-chloro-3-fluoro-phenyl | 4-chloro-3-fluoro-phenyl | 2-acetoxyethyl | 2.4 | 2 |
| 1661 | 4-chloro-3-fluoro-phenyl | 4-chloro-3-fluoro-phenyl | methylcarboxyl | 24 | 32 |
| 1662 | 4-fluoro-3-nitro-phenyl | 4-fluoro-3-nitro-phenyl | 2-acetoxyethyl | 2.1 | 1 |
| 1663 | 4-fluoro-3-nitro-phenyl | 4-fluoro-3-nitro-phenyl | methylcarboxyl | 3.1 | 4 |
| 1664 | 3,4,5-trifluoro-phenyl | 3,4,5-trifluoro-phenyl | 2-acetoxylethyl | 2.8 | 4 |
| 1665 | 3,4,5-trifluoro-phenyl | 3,4,5-trifluoro-phenyl | methylcarboxyl | 5.0 | 8 |
| 1666 | 4-chloro-3-trifluoromethyl-phenyl | 4-chloro-3-trifluoromethyl-phenyl | 2-acetoxyethyl | 1.3 | 1 |

The solubility in aqueous media of compounds of the invention of which $R^5$ is acyl (that is, —$COR^6$) is substantially independent of pH.

Particularly preferred compounds of the invention are compounds nos. 1561, 1562, 1567, 1570, 1571, 1586, 1591, 1600, 1612, 1618, 1622, 1625, 1643, 1644, 1647, 1648, 1649, 1652, 1653, 1656, 1657, 1658, 1662. Most preferred compounds of the invention are compounds nos. 1570, 1571, 1625, 1662.

Since the compound of the invention comprises a 1,5-disubstituted 1,4-pentene-3-one moiety it can exist in four cis/trans isomers EE, ZE, ES, ZZ. In defining the compound of the invention this isomerism is defined in the foregoing as "$R^1$, $R^2$ at double bond d1 and $R^3$, $R^4$ at double bond d2 can, independent of each other, have a configuration opposite to that of formula S1". The compound of the invention comprises any such isomer and any mixture of such isomers.

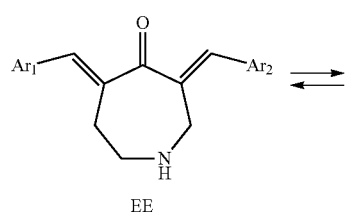

EE

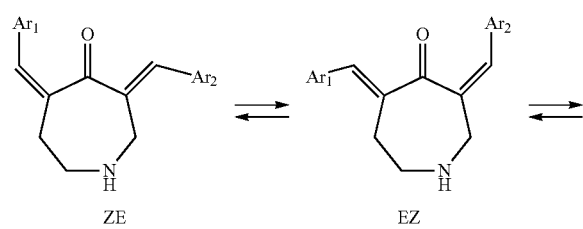

ZE        EZ

-continued

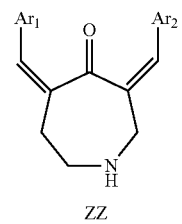

ZZ

In synthesis the compound of the invention is obtained as a mixture of isomer but sometimes also in form of the isomer with the lowest solubility in the particular solvent, from which it precipitates or crystallizes. While pure isomers thus can be obtained under controlled conditions, the pharmacological effect of the compound is exhibited by all isomers. The reason for this is their equilibration in the presence of water or other hydroxylic or sulfhydrylic solvent or agent, which is accelerated by acid and base catalysis.

Accordingly, the term "compound of the invention" as used herein comprises a pure isomer of the aforementioned kind as well as a mixture of two or more such isomers. The rate of equilibration of the compound of the invention in aqueous body fluid is sufficient to provide for substantial equilibration within a single treatment period.

The compound of the invention comprises an azepane moiety, preferably an azepane-4-one moiety. According to an important aspect of the invention, the compound of the invention exhibits a cytotoxic activity superior to that of a structurally corresponding compound comprising a piperidine moiety, such as a 4-piperidinone moiety.

According to another important aspect of the invention, the compound of the invention comprising an azepane moiety, in particular an azepan-4-one moiety exhibits a solubility in a liquid carrier suitable for administration to a patient, such as dimethyl sulfoxide, superior to that of a structurally corresponding compound comprising a piperidine moiety, such as a 4-piperidinone moiety.

A "single treatment period" is the period of time elapsing between administration and consumption of the compound of the invention, that is, the point in time at which the concentration of the compound of the invention at a site of action, such as in a tumor, has been reduced by 90% or 95% or 99% and more. In a pharmaceutical composition, an isomer or a mixture of isomers of the compound of the invention is stabilized against isomerization by careful exclusion of moisture.

The method of the invention comprises administering to the patient in need a pharmacologically effective dose of the compound of the invention in a suitable pharmaceutical carrier, such as, for instance, dissolved or suspended in an aqueous carrier or in a carrier comprising dimethyl sulfoxide or N,N-dimethylacetamide. Administration can be by any suitable route, such as by intravenous, intramuscular, intraperitoneal or subcutaneous injection or infusion. Other methods of administration, in particular per os, are also contemplated, such as in form of tablets or hard or soft gelatin capsules.

The person skilled in the art knows how to determine a pharmacologically effective dose. Such a dose may be from 0.0001 g/kg to 0.1 g/kg body weight, in particular from 0.001 g/kg to 0.01 g/kg kg body weight, consideration being given to whether the agent is administered systemically or locally.

Consistent with DUB inhibition, treatment with the compound of the invention causes the accumulation of polyubiquitinated proteins of higher molecular weight in comparison with bortezomib treatment, and results in a stronger unfolded protein response. According to the invention, it has also been found that apoptosis induction by the compound of the invention differs from that of bortezomib by being insensitive to disruption of the p53 tumor suppressor and insensitive to overexpression of the apoptosis inhibitor Bcl-2.

According to the present invention treatment with the compound of the invention inhibits tumor progression in human and mouse tumor in vivo models of breast, lung, colon, head & neck carcinoma, and inhibits infiltration in an acute myeloid leukaemia (AML) model. In consequence, inhibiting the DUB activity of the 19S RP by the compound of the invention is disclosed to be a viable option for the treatment of cancer in humans and animals. Thus, more specifically, is disclosed a method of treating in a person a cancer tumor refractory to state-of-the-art chemotherapy comprising administering, in a pharmaceutically acceptable carrier, a pharmacologically effective dose of the compound of the invention. The method of the invention is particularly useful in the treatment of a patient having a tumor of which cells are refractory to treatment due to over-expression of the intrinsic apoptosis-inhibitor Bcl-2.

According to a preferred aspect of the invention the 19S RP DUBs comprise UCHL5 and USP14. According to another preferred aspect of the invention the deubiquitinating (DUB) activity of non-proteasomal DUBs is not affected by the compound of the invention. The compound of the invention can be administered dissolved or suspended in a liquid carrier by any suitable route, such as by intravenous, intramuscular and subcutaneous administration. Alternatively or additionally, the compound of the invention can be administered perorally, such as in form of a tablet or capsule. A useful pharmacologically effective dose of the compound of the invention is from 0.0001 g/kg to 0.1 g/kg body weight, in particular from 0.001 g/kg to 0.01 g/kg kg body weight, consideration being given to whether the compound is administered systemically or locally. The method may comprise selecting a person to be treated by determining the growth rate of the cancer prior to and upon administration of bortezomib or said active principle sharing the mechanism of deubiquitinating activity inhibition of bortezomib or said other anti-cancer drug, a positive growth rate, in particular a growth rate of more than 5% or more than 10% or more than 25% per month constituting a selection marker.

The compound of the invention blocks cellular proteasome function, as confirmed by use of a reporter cell line, which expresses ubiquitin tagged to yellow fluorescent protein (UbG76V-YFP) constitutively targeted for proteasomal degradation (12). Immunoblotting and flow cytometry revealed a dose dependent accumulation of the Ub-YFP reporter (IC50=0.8 μm) suggesting an impairment of proteasome function. Since inhibition of proteasome function is characterized by defects in ubiquitin turnover (13) colon carcinoma HCT116 cells were treated with the compound of the invention and the level of ubiquitin conjugation analyzed by immunoblotting. The treatment caused the rapid time dependent accumulation of polyubiquitinated proteins of a higher molecular weight in comparison with the 20S CP inhibitor bortezomib, suggesting that the compound of the invention inhibits an alternative branch of the UPS. The increase in polyubiquitin is associated with a strong proteotoxic response characterized by induction of HSPA6 (Hsp70B'), HSPA1B and DNA1B1 (Hsp40).

The turnover of many cell cycle regulatory proteins is controlled by the UPS including inhibitors of the cyclin-dependent kinase $p21^{Cip1}$, $p27^{Kip1}$ and the tumor suppressor p53 (4). Treatment with the compound of the invention increases their levels in a dose dependent manner without altering the levels of ornithine decarboxylase 1 (ODC1), an ubiquitin-independent proteasome substrate (8). The increase in cell cycle regulators was concomitant with growth arrest in the G2/M phase boundary and increased sub G1 DNA content. The cell cycle arrest observed is not associated with increased levels of DNA damage markers such as phosphorylated p53 (at Ser 15) (9) or H2AX (at Ser 139) (10), suggesting that b-AP15 is not a genotoxic agent.

The increase in sub G1 DNA, caspase-3 activation and cleavage of poly-ADP ribose polymerase (PARP) and cytokeratin is associated with an overall decrease in cell viability at drug concentrations that induce the accumulation of polyubiquitin connecting UPS inhibition and apoptosis. Apoptosis induction by bortezomib is sensitive to the status of the p53 tumor suppressor and over-expression of the anti-apoptotic Bcl-2 oncoprotein (11, 12). By using isogenic clones of HCT116 colon cancer cells it was demonstrated that b-AP15 induced apoptosis is insensitive to over-expression of Bcl-2 and disruption of the apoptotic regulators p52, BAX or PUMA. Measurement of cytotoxic activity shows that the compound of the invention is more toxic to the colon carcinoma cell line HTC-116 than to immortalized retinal pigment epithelial cells (hTERT-RPE1) and peripheral blood mononuclear cells (PBMC). The compound of the invention exhibits a higher degree of cytotoxic activity towards the HTC-116 cells than towards normal cell types.

The observed reduction in cellular proteasome activity cannot be explained by inhibition of proteolytic activities of the β subunits of the 20S CP. In vitro experiments using activity-specific substrates do not show inhibition in any of the proteolytic activities of the 20S CP or 26S proteasome, disassociation of the 19S RP and 20S CP or inhibition of polyubiquitin binding to the proteasome.

The compound of the invention comprises an α-β dienone entity with two sterically accessible g carbons. A structurally similar pharmacophore has been earlier described to be comprised by a class of ubiquitin isopeptidase inhibitors (13). However, when cellular DUB activity was tested using ubiquitin 7-amido-4-methylcoumarin (Ub-AMC) on treated cells treated with the compound of the invention, no reduction in Ub-AMC cleavage was observed. This demonstrates that the compound of the invention is not a general DUB inhibitor. While not wishing to be bound by theory, the similarities in pharmacophore structure and the data showing that compound of the invention inhibits proteasome activity independent of the 20S CP indicate that the compound of the invention inhibits the proteasome by blocking the deubiquitinating activity of the 19S RP.

In vitro assays using Ub-AMC and purified 19S RP or 26S proteasomes confirmed that the compound of the invention inhibits the deubiquitinating activity of both the 19S RP and 26S proteasome. Recombinant ubiquitin-GFP is a substrate for 19S RP DUB activity (15). Treatment of 19S RP with b-AP15 efficiently inhibited the cleavage of Ub-GFP and ubiquitinated HDM2. The type of ubiquitin bonds present in the polyubiquitin chain determines the fate of an ubiquitin-modified substrate.

K48 linked polyubiquitin chains generally target conjoined proteins for degradation (14), whereas K63 linked chains are involved in non-proteolytic roles including DNA repair (15) and mitotic chromosome segregation (16). Ubiquitin chain disassembly reactions revealed that the compound of the invention inhibits 19S RP processing of both K48 and K63 linked ubiquitin tetramers. The inhibition of ubiquitin chain disassembly observed may account for the accumulation of high molecular weight ubiquitin conjugates in cells treated with the compound of the invention.

The deubiquitinating activity of the proteasome is attributed to the action of three DUBs, UCHL5, USP14 and POH1, all localized within the 19S RP (17-19). Both UCHL5 and USP14 are sensitive to N-ethylmaleimide (NEM), a general inhibitor of cysteine proteases, whereas POH1 is insensitive to inhibition by NEM but sensitive to metal chelators such as N,N,N,N-tetrakis-(2-pyridylmethyl)ethylenediamine (TPEN) (20). Inhibition experiments showed that residual DUB activity is present even after co-treatment of 19S RP with NEM and the compound of the invention. This residual DUB activity was abolished upon co-treatment of 19S RP with the compound of the invention and TPEN, suggesting that the compound of the invention primarily inhibits one or both of the NEM sensitive cysteine DUBs. The β-carbons of the compound of the invention may serve as Michael acceptor moieties, resulting in covalent binding to cysteine residues in target proteins. In vitro assays showed, however, that the compound of the invention is a reversible inhibitor and that glutathione does not preclude the inhibitory activity of the compound.

To identify specifically which DUBs were inhibited by treatment with the compound of the invention, competitive labelling experiments were performed using hemagglutinin tagged ubiquitin vinylsulphonone (HA-UbVS), an active site directed probe that irreversibly reacts with DUBs of the cysteine class (17). Incubation of 19S RP or 26S proteasomes with the compound of the invention abolished Ub-VS labelling of two DUBs of molecular weights corresponding to UCHL5 and USP14. A similar result was obtained using UbVs on lysates derived from drug-treated cells. Immunoblot analysis showed a downward shift in molecular weight of both USP14 and UCHL5 due to loss of activity and decreased UbVs labelling. This is consistent with affinity-purified proteasomes from the compound of the invention treated cells displaying reduced DUB activity confined to the proteasome and not evident in cell lysates. Additional in vitro assays showed minimal inhibition of the compound of the invention on recombinant non-proteasomal cysteine DUBs, consistent with the notion that inhibition is not due to general cysteine reactivity.

The compound of the invention does substantially decrease and even stop tumor growth in vivo, as shown by its administration to mice bearing either a human tumor or mouse xenografts. When the compound of the invention is administered daily to SCID mice bearing FaDu head and neck carcinoma xenografts, significant inhibition of FaDu tumor growth is observed following daily treatment with the compound of the invention (treated/control tumor volume, T/C=0.4, p=<0.001). Tumor cell death was analyzed by measuring xenograft derived cytokeratin (CK18) in circulation. Cytokeratin-18 is a biomarker for apoptosis (21, 22); a significant increase in plasma levels of total human CK18 was observed (p=0.01). Levels of caspase cleaved CK18 (CK18-Asp396) increased moderately compared with total levels, suggesting that the compound of the invention has activity against tumor cells in vivo. The compound of the invention was also shown to inhibit tumor onset of HCT-116$^{Bcl2+}$ colon carcinoma xenografts in nude mice, as demonstrated by significant delay in tumor onset in comparison to vehicle treated controls. Similarly, the compound of the invention inhibits tumor growth in syngenic mice models using less frequent administration schedules.

Ubiquitin C-terminal hydrolases (UCH) and ubiquitin specific proteases (USP) are major subgroups of the approximately one hundred DUBs encoded by the human genome (23). The mechanism of specificity of the compound of the invention for UCHL5 and USP14 in the 19S RP may be related to unique conformations of these enzymes in the 19S RP or due to drug-induced alterations of the 19S RP structure. The present findings are consistent with reports in the art indicating that loss of both UCHL5 and USP14, unlike loss of either one alone, leads to the accumulation of polyubiquitinated proteins and inhibition of cellular protein degradation (24).

The observation that DUB inhibition is associated with high molecular weight ubiquitin-substrate complexes seems to be of particular relevance. Strong expression of chaperone genes was observed in cells treated with the compound of the invention, indicating induction of a proteotoxic response. High-molecular weight ubiquitin-substrate complexes accumulating as a result of DUB inhibition by the compound of the invention seem to generate strong cytotoxicity.

In the following the invention will be described in greater detail by reference to preferred embodiments thereof illustrated by a drawing comprising a number of figures.

DESCRIPTION OF PREFERRED EMBODIMENTS

Methods

Figure 1A:
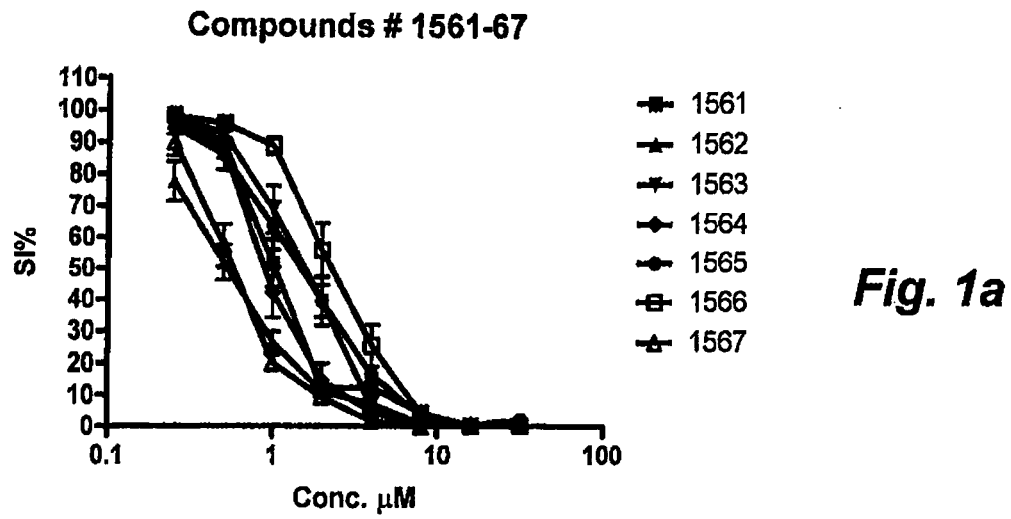
FIGS. 1a to 1o are diagrams illustrating induction of dose-dependent cytotoxicity after 72 hours of continuous compound exposure to the reporter cell line HCT-116 by embodiments of the compound of the invention, as measured FMCA (Fluorometric Microculture Cytotoxicity Assay), as well as absence of such induction by structurally related compounds not comprised by the invention. Treated cells were compared to untreated controls (survival index)
Figure 1B:
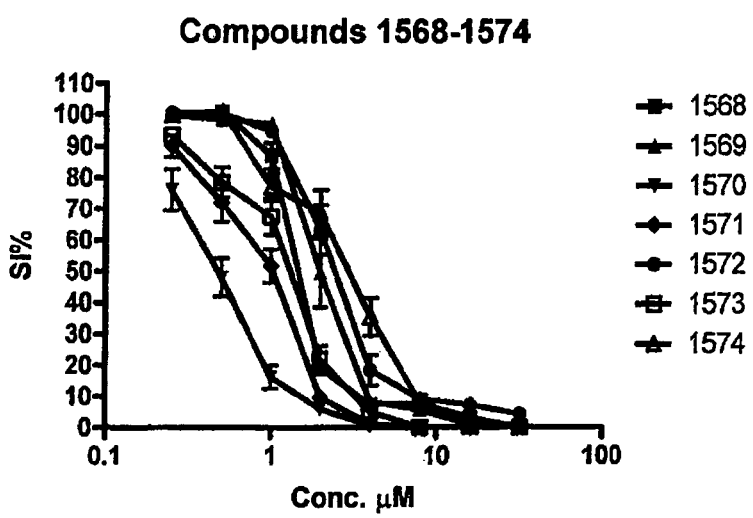
Figure 1C:
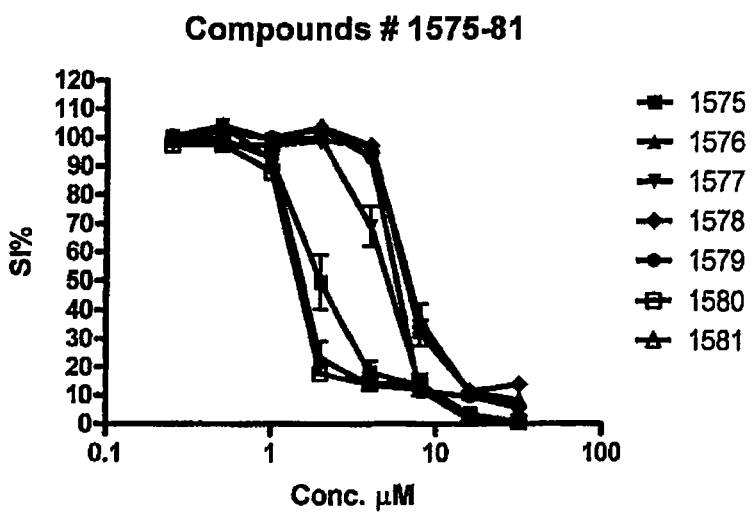
Figure 1D:
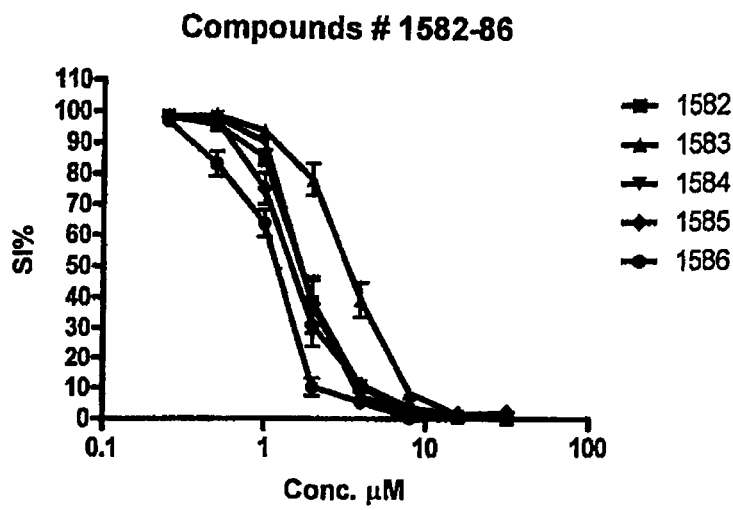
Figure 1E:
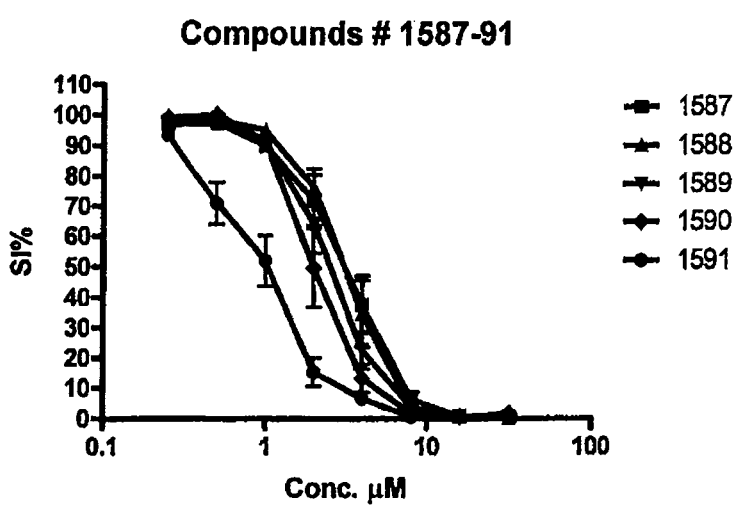
Figure 1F:
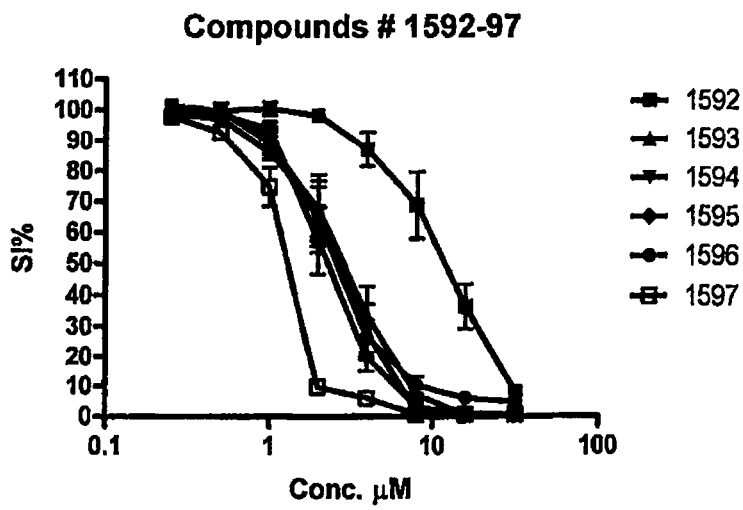
Figure 1G:
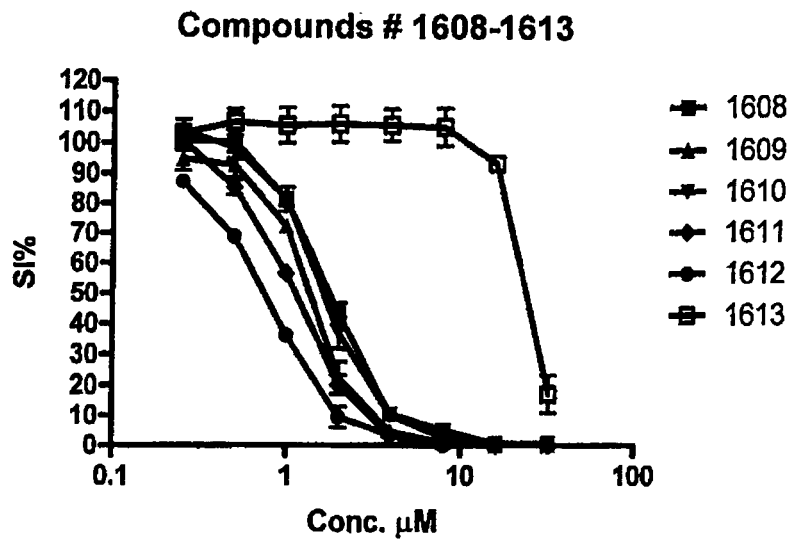
Figure 1H:
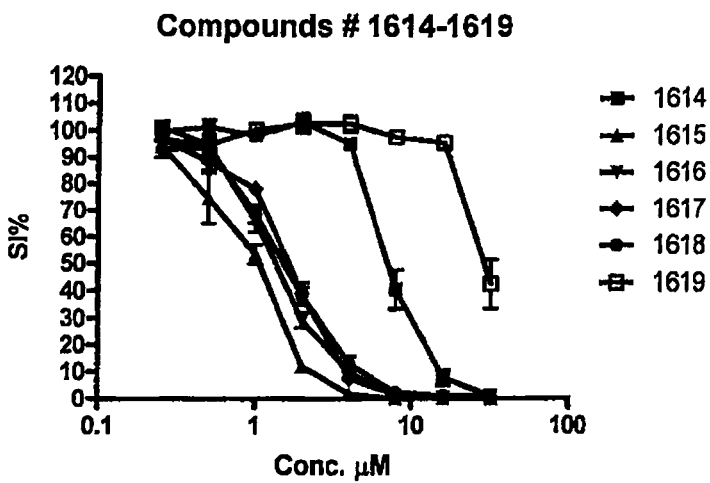
Figure 1I:
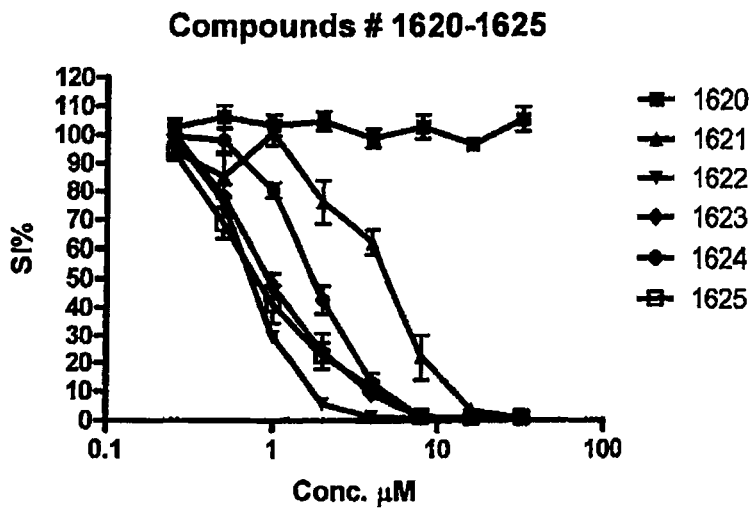
Figure 1M:
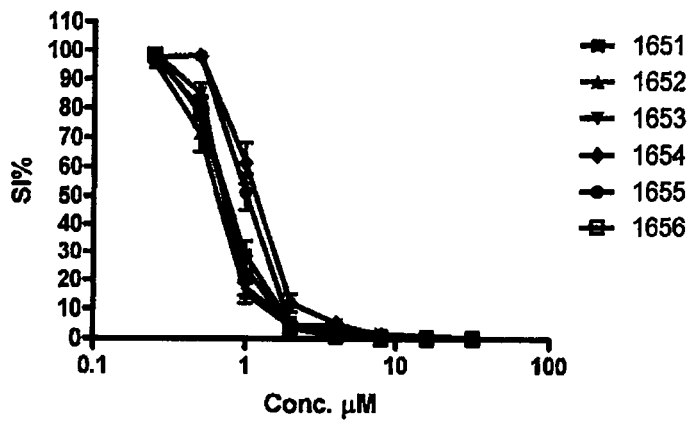
Figure 1N:
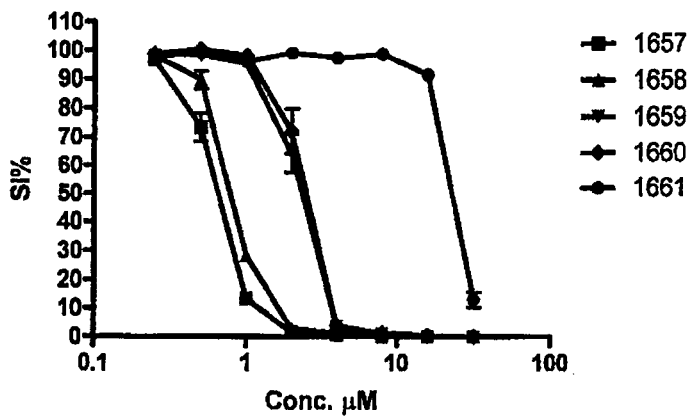

In vitro proteasome activity assays are performed in black 96-well microtiter plates using human 20S proteasome (Boston Biochem) in reaction buffer (25 mM Hepes, 0.5 mM EDTA, 0.03% SDS) with Suc-LLVY-AMC, Z-LLE-AMC or Boc-LRRAMC used as substrates for proteasome activity. De-ubiquitinase activity assays are performed with human 19S RP (Boston Biochem) with ubiquitin-AMC as substrate. For FaDu xenograft studies a 100-µl-cell suspension containing $1\times10^6$ cells is injected subcutaneously into the flank of SCID. Upon tumor take mice are randomized into control or treatment groups and administered with 5 mg kg$^{-1}$ compound of the invention or vehicle. In vivo levels of apoptosis and cell death are determined from the detection of caspase cleaved and total levels of cytokeratin-18 in plasma using M30 Apoptosense® and M65 ELISA®s assays (Peviva). The methods are described below in more detail.

Reagents. Reagents were obtained from the following sources: 20S proteasome (E-360), 26S proteasome (E-365), 19S proteasome (E-366), Suc-LLVY-AMC (S-280), Z-LLE-AMC (5-230), Boc-LRR-AMC (S-300), Ubiquitin-AMC (U-550), Tetra-ubiquitin K63 (UC-310), Tetra-ubiquitin K48 (UC-210), deconjugating enzyme set (KE10), HA-Ubiquitin Vinyl Sulfone (U-212) (Boston Biochem); anti-β-actin (AC-15), ODC-1 (HPA001536) (Sigma Aldrich); anti-LC-3 (2775), anti-GAPDH (2118), anti-p44/42 MAPK (4695), anti-Phospho-p44/42 MAPK (9101)(Cell Signaling); N-ethylmaleimide (34115) (EMD Chemicals); anti-Ubiquitin K48 (Apu2), anti-Ubiquitin (MAB1510) (Millipore); anti-p53 (DO1), anti-UCHL5 (H-110), Hdm2 (SMP14) (Santa Cruz); anti-PARP (C2-10), anti-p27 (G173-524), anti-active Caspase 3 (C92-605) (BD Biosciences); anti-USP14 (A300-919A) (Bethyl Laboratories); anti-HA (12CA5) (Roche). Bortezomib was obtained from the Department of Oncology, Karolinska Hospital, Sweden.

Cell culture. MCF7 cells are maintained in MEM/10% fetal calf serum. HCT-116 p53+/+, p53−/−, Bcl-2+/+, PUMA−/− and BAX−/− cells are maintained in McCoy's 5A modified medium/10% fetal calf serum. The HCT-116 p53+/+, p53−/−, PUMA−/− and BAX−/− are generated as described (25). The HCT-116 Bcl-2+/+ cell line was generated by transfecting parental HCT-116 p53+/+ cells with pCEP4 Bcl-2 (Addgene plasmid 16461) (26) and isolating high expression clones. FaDu and LLC3 cells are maintained in DMEM high glucose medium supplemented with 10% fetal calf serum, Na pyruvate, Hepes and non-essential amino acids. 4T1.12B carcinoma cells are maintained in RPMI medium supplemented with 10% fetal calf serum. The proteasome reporter cell line MelJuSo Ub-YFP was generated as described (12). Cells were maintained in Dulbecco's Modified Eagle's Medium/10% fetal calf serum. The retinal epithelial cell line was generated as described (12). All cells are maintained in Dulbecco's Modified Eagle Medium/10% fetal calf serum. The retinal epithelial cell line was generated as described (28). All cells are maintained at 37° C. in 5% $CO_2$.

Proteasome and DUB inhibition assays. In vitro proteasome activity assays using 20S CP (2 nM) (Boston Biochem) are performed at 37° C. in 100-µl reaction buffer (25 mM Hepes, 0.5 mM EDTA, 0.03% SDS). Samples are incubated for 10 min with indicated compound followed by addition of 10 µM Suc-LLVY-AMC, Z-LLE-AMC or Boc-LRR-AMC for the detection of chymotrypsin-like, caspase-like and trypsin-like activity respectively. For DUB inhibition assays 19S RP (5 nM), 26S (5 nM) UCH-L1 (5 nM), UCH-L3 (0.3 nM), USP2CD (5 nM) USP7CD (5 nM) USP8CD (5 nM) and BAP1 (5 nM) are incubated with the compound of the invention followed by addition of ubiquitin-AMC (1000 nM). Fluorescence is monitored using Wallac Multilabel counter or Tecan Infinite M1000 equipped with 360 nm excitation and 460 nm emission filters.

Substrate overlay assays. Native gel electrophoresis is performed as described (29). In brief 4 µg of purified 26S proteasome (Boston Biochem) is mixed with 10 or 50 µM of the compound of the invention and incubated at 37° C. for 10 min. Samples are resolved on 4% non-denaturing PAGE. Gels are submerged in assay buffer (20 mM Tris-HCL, 5 mM $MgCl_2$, 1 mM ATP, 0.1 mM Suc-LLVY-AMC) and proteasomes are visualized under UV illumination.

Ubiquitin-cleavage assay. The recombinant Ub-GFP plasmid pet19b Ub-M-GFP is generated as described (30). In brief recombinant Ub-GFP is purified from BL21 E. coli cells by His affinity purification. For cleavage assays 19S RP (25 nM) is incubated with 10 mM NEM, 250 µM TPEN or 50 µM of the compound of the invention for 10 min followed by the addition of recombinant Ub-GFP (200 nM). Ubiquitin chain disassembly reactions are performed essentially as above except K48- or K63-linked ubiquitin tetramers (50 ng) are substituted for Ub-GFP. The level of Ub-GFP cleavage or ubiquitin disassembly is determined by immunoblotting with anti ubiquitin antibodies. The ubiquitinated Hdm2 substrate is generated according to the Boston Biochem protocol (K-200). For the cleavage assay 19S RP (25 nM) is incubated with 50 µM of the compound of the invention or DMSO for 10 min followed by the addition of ubiquitinated Hdm2 substrate (100 nM). The cleavage of ubiquitinated Hdm2 substrate and ubiquitinated Hdm2 is determined by immunoblotting with anti-Hdm2 antibodies.

Proteasome isolation: HCT-116 cells are treated with bortezomib (100 nM) or the compound of the invention (1 µM) for 3 hours. After stimulation, the cells are lysed in 50 mM HEPES pH 7.4, 250 mM sucrose, 10 mM $MgCl_2$, 2 mM ATP, 1 mM DTT and 0.025% digitonin. Samples are sonicated briefly and incubated for 15 min on ice. Proteasomes from these samples are isolated according to the manufacturer's protocol.

UbVS labelling of DUBs. For labelling of DUBs in cell lysates sub confluent cells are harvested by trypsinization, washed three times with PBS, and centrifuged at 1500 RPM for 5 min. Cell pellets are lysed with buffer (50 mM HEPES pH 7.4, 250 mM sucrose, 10 mM $MgCl_2$, 2 mM ATP, 1 mM DTT) on ice for 15 min. Debris is removed by centrifugation and 25 µg of protein is labelled with 1 µM HA-UbVS for 30 min at 37° C. Samples are resolved by SDS-PAGE and analyzed by immunoblotting with indicated antibodies.

Figure 1O:
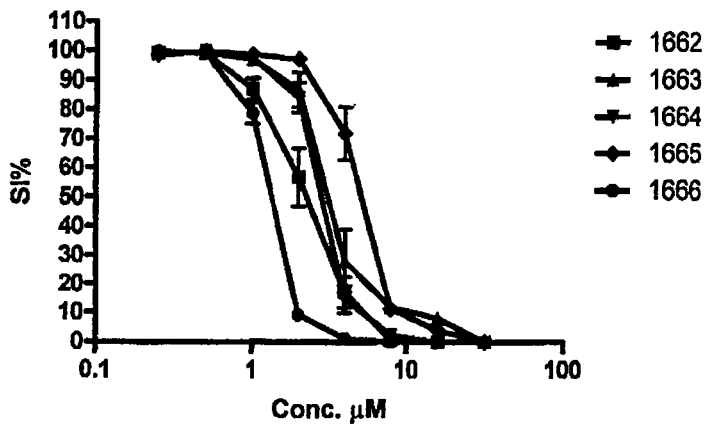
Figure 2A:
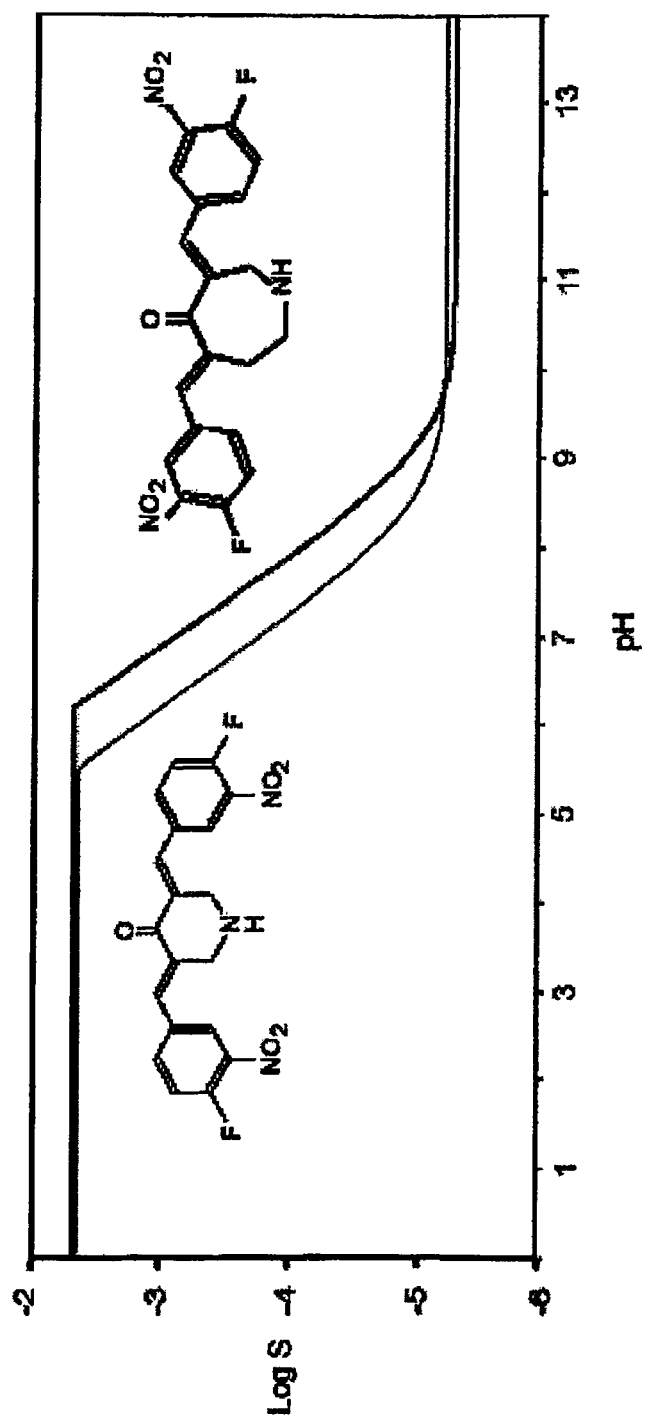
FIGS. 2a to 2e are diagrams illustrating the superior solubility of compounds of the invention in an aqueous media at physiological pH.
Figure 2B:
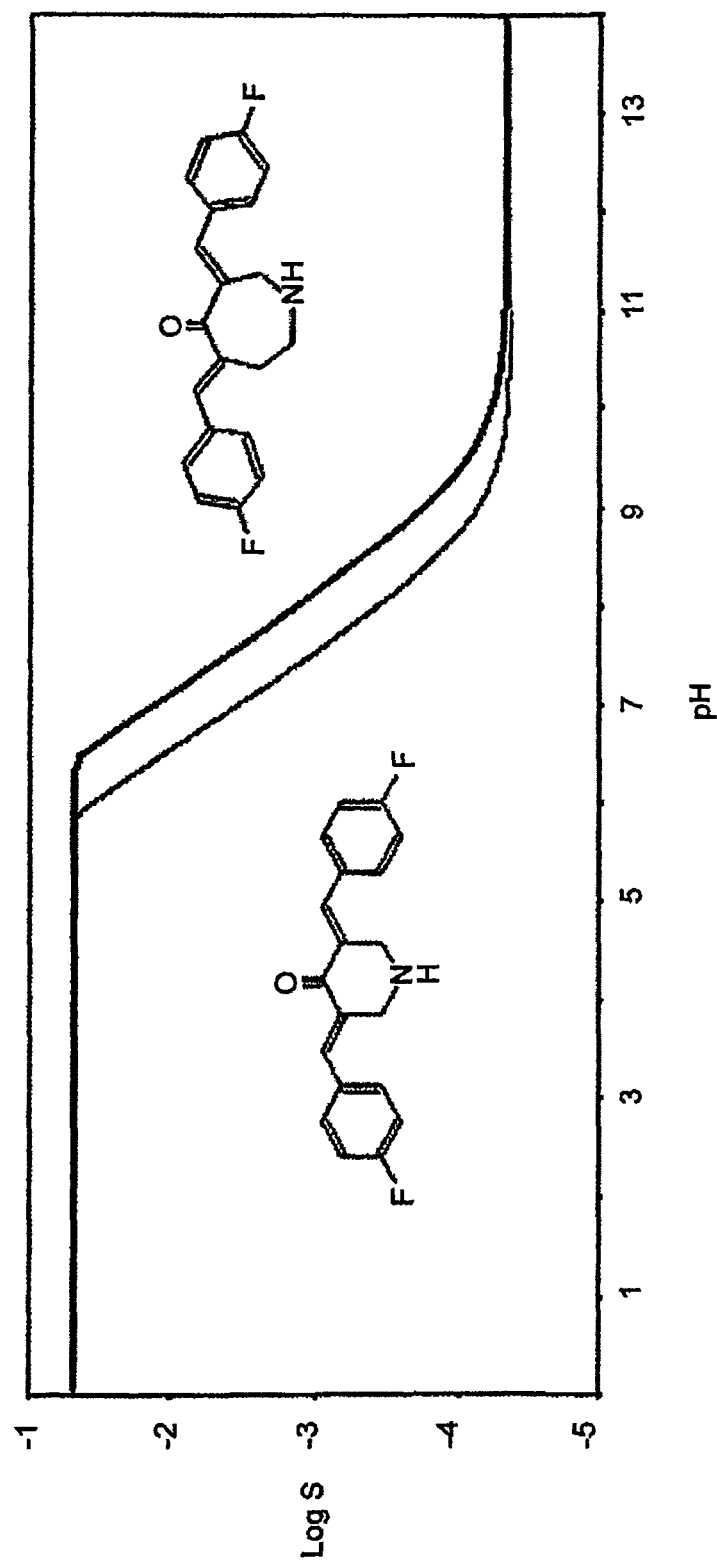
Figure 2C:
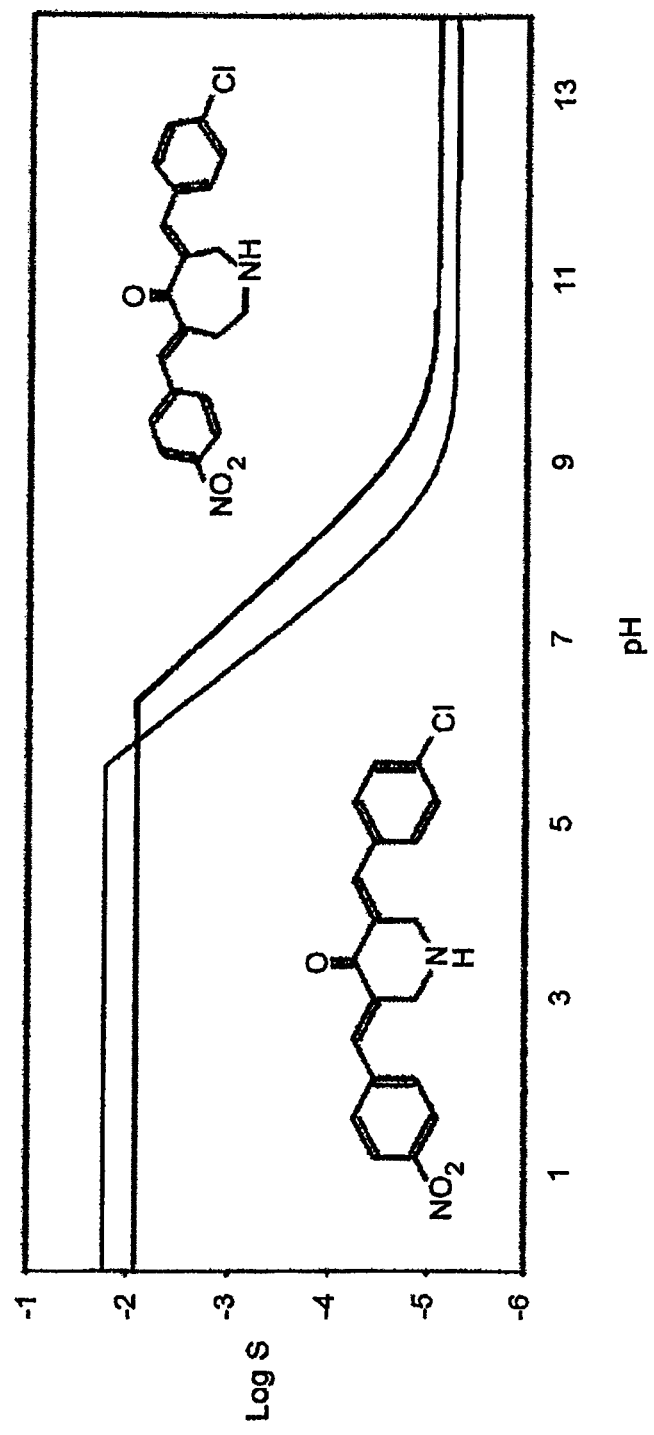
Figure 2D:
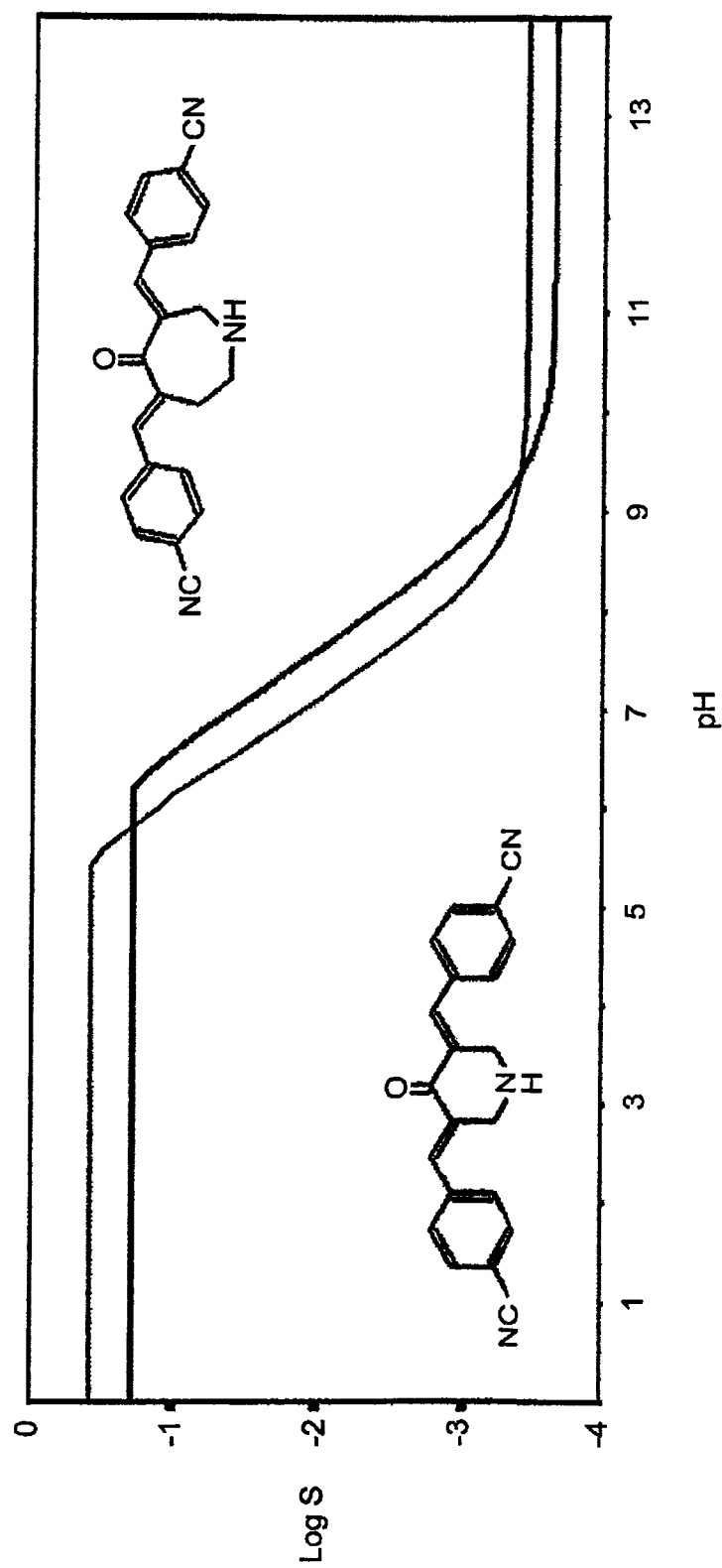
Figure 2E:
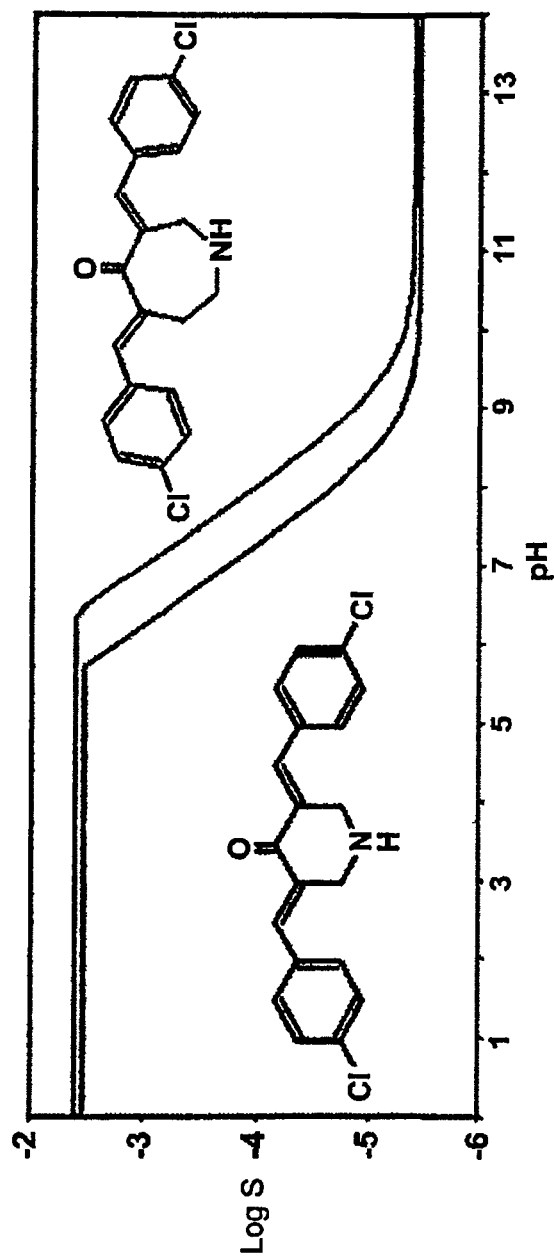

Determination of cell apoptosis and viability. For determination of apoptosis parental HCT-116 p53+/+ cells are treated with the increasing doses of the compound of the invention for 24 h. Treatment doses are based on the drug concentration that resulted in maximal apoptosis over a 24 h period. HCT-116 cells are seeded in 96-well microtiter plates at 10,000 cells per well and incubated overnight. Cells are treated with indicated drug for 24 h. At the end of the incubation period, NP40 is added to the tissue culture medium to 0.1% and 25 µl of the content of each well was assayed using the M30-Apoptosense® ELISA as previously described (31). Cell viability is determined by measuring acid phosphatase activity or using the FMCA method (32). For the acid phosphatase activity cells are seeded at 5000 cells per well in 96-well culture plates and incubated for 12 h at 37° C. Compounds are added to the cells in growth media and incubated for 72 h at 37° C. Cells are washed with 200 µl warm PBS. 100 µl of para-nitrophenyl phosphate (pNPP, 2 mg/ml) in Na acetate buffer pH 5 (NaAc 0.1 M, 0.1% Triton-X-100) is added per well. Cells are incubated for 2 h after which reaction was stopped by addition of 1N NaOH. Absorbance is measured at 405 nm. The dose-dependent cytotoxicity of a number of embodiments of the compound of the invention is illustrated in FIGS. 1a-1o.

For the FMCA assay cells are seeded in the drug-prepared 384-well plates using the pipetting robot Precision 2000 (Bio-Tek Instruments Inc., Winooski, Vt.). The plates are incubated for 72 h and then transferred to an integrated HTS SAIGAN Core System consisting of an ORCA robot (Beckman Coulter) with $CO_2$ incubator (Cytomat 2C, Kendro, Sollentuna, Sweden), dispenser module (Multidrop 384, Titertek, Huntsville, Ala.), washer module (ELx 405, Bio-Tek Instruments Inc), delidding station, plate hotels, barcode reader (Beckman Coulter), liquid handler (Biomek 2000, Beckman Coulter) and a multipurpose reader (FLUOstar Optima, BMG Labtech GmbH, Offenburg, Germany) for automated FMCA. Survival index (SI) is defined as the fluorescence of test wells in percentage of controls with blank values subtracted.

Cell-cycle analysis. For determination of cell cycle HCT-116 cells are treated with the compound of the invention or DMSO cells are harvested by trypsinisation, washed and fixed in 70% ice cold EtOH for 12 h. The cells are re-suspended in staining solution containing propidium iodide (50 μg/ml) and RNAse A (0.5 μg/ml) in PBS. Samples are run on BD FACScalibur. The percentage of cells in each phase of the cell cycle is determined using ModFit software.

EXAMPLE 1

Exemplary Synthesis of Preferred Embodiments to the Compound of the Invention

General information. All solvents used were of HPLC grade or better. When anhydrous conditions were required, an excess of 3 Å molecular sieves were added to the solvent at least 24 h before use to ensure dryness. $^1$H NMR nuclear magnetic resonance (NMR) was recorded on a Bruker Advance DPX 400 spectrometer at 400.1 MHz. Low resolution electrospray ionization mass spectra were obtained using an Agilent mass spectrometer in positive ionization mode. Flash chromatography was performed on Merck silica gel 60 (230-400 mesh). Analytical LCMS data were obtained with an Agilent mass spectrometer; Agilent 1100 system; A: ACE C8 column (50×3.0 mm, 5 μM); gradient: 10-97% acetonitrile in water/0.1% TFA, in 3 min 1.0 mL/min, or B: xBridge C18 column (3.5 μM. 50×3.0 mm), gradient 10% to 97% acetonitrile in 10 mM $NH_4HCO_3$ (pH 10) in 3 min, 1 mL/min). Names of chemical structures were determined using Marvin Scech 5.2.6, ChemAxon.

(3E,5E)-3,5-Bis(phenylmethylidene)azepan-4-one (#1516) and (3E,5E)-3,5-bis(4-methoxyphenylmethylidene)-azepan-4-one (#1517)

Hexahydro-4H-azepin-4-one (0.45 g, 3.0 mmol), together with either benzaldehyde (0.70 g, 7.0 mmol), 4-methoxybenzaldehyde (0.90 g, 7.0 mmol) or 4-chlorobenzaldehyde (0.92 g, 7.0 mmol) was dissolved in acetic acid (10 mL). Then sulfuric acid (conc. 1 mL) was added drop-wise and the reactions were stirred for 24 hours at rt. Water (30 mL) was added and the precipitate filtered and dried in vacuo over night. No further purification was performed. Compound #1516 was obtained with 99% purity determined by LCMS (System A) MS ESI$^+$ m/z 290 [M+H]$^+$. Compound #1517 was also obtained in 99% purity determined by LCMS (System A), MS ESI$^+$ m/z 350 [M+H]$^+$. Compound #1518 was obtained in 91% purity; LCMS (System A). MS ESI$^+$ m/z 358 [M]$^+$, 360 [M+2]$^+$.

(3E,5E)-3,5-bis(phenylmethylidene)-1-(prop-2-enoyl)-azepan-4-one (#1520)

(3E,5E)-3,5-Bix(phenylmethylidene)azepan-4-one (#1516) (50.0 mg, 0.182 mmol) and acrylic acid (14.4 mg, 0.20 mmol), HBTU (58.4 mg, 0.182 mmol), triethylamine (36.7 mg, 0.364 mmol) were dissolved in DMF (2 mL) and stirred over night. Ethyl acetate and brine were added and the products were extracted. The combined organic layers were dried and evaporated. The crude product was diluted with methanol and purified by preparative HPLC. Compound #1520 was obtained in 96% purity, MS-ESI$^+$ m/z 344 [M+H]$^+$.

(2R)-[(3E,5E)-3,5-Bis(4-nitrophenylmethylidene)-4-oxo-1-(pyrrolidin-2-yl-carbonyl)-azepan trifluoroacetate (#1505)

N-Boc-azepanone (100 mg, 0.47 mmol) and 4-nitrobenzaldehyde (156 mg, 1.03 mmol) were dissolved in acetic acid (10 mL). Then sulfuric acid (conc. 1 mL) was added dropwise and the reactions were stirred at room temperature for three days. Then more aldehyde and sulfuric acid were added and the reaction stirred another 24 hours, more acid was added twice 24 hours apart. The reaction was quenched by addition of water and the precipitated crude intermediates were filtered off and washed with water. After drying the product in vacuo over night 2×35 mg (0.09 mmol) of the crude intermediate was weighed into two flasks and dissolved together with monoethyl succinate (14.8 mg, 0.10 mmol) in DCM/DMF (2 mL, 4:1). Triethylamine (19.3 μL, 0.14 mmol) was added and the mixture stirred for 5 min before addition of HATU (38.6 mg, 0.10 mmol). After continuing stirring for 12 hours more triethylamine and HATU was added and the stirring continued for 4 hours. The solvents were evaporated and the residue purified by preparative HPLC. The residue was dissolved in dichloromethane/trifluroacetic acid (5 mL, 4:1), stirred for 40 min and concentrated again. Compound #1505 was obtained in 93% purity by LCMS (System A). MS ESI+ m/z 477 [M+H]$^+$.

EXAMPLE 2

Further Exemplary Syntheses of Preferred Embodiments of the Compound of the Invention (2R)-2-{[(3E,5E)-3,5-bis[(4-nitrophenyl)methylidene]-4-oxoazepan-1-carbonyl}pyrrolidinium trifluoroacetate (compound #1505). N-boc Azepan-4-one (0.10 g, 0.47 mmol) and 4-nitrobenzaldehyde (156 mg, 1.0 mmol) were dissolved in acetic acid (10 mL), conc. $H_2SO_4$ (1 mL) was added dropwise and the reaction stirred at rt over the weekend. More aldehyde (156 mg) and $H_2SO_4$ (1 mL) were added and stirring continued at rt over night. Another mL conc. $H_2SO_4$ was added and reaction stirred over night again. Conc. $H_2SO_4$ was added once more and the reaction stirred until complete (for two weeks). Upon addition of water a brown precipitate was formed, filtered off, washed with water, and dried under vacuum to give 339.5 mg of brown solid Intermediate 1, which was used without further purification. Intermediate 1 (35 mg, 0.09 mmol) and N-boc proline (22 mg, 0.10 mmol)

were dissolved in DCM/DMF (4:1, 2 mL). TEA (19 µL, 0.14 mmol) was added and the mixture stirred for 5 min, then HATU (38.6 mg, 0.10 mmol) was added and the reaction stirred at rt overnight. More TEA (19 µL, 0.14 mmol) and HATU (38.6 mg, 0.10 mmol) was added, and the reaction stirred for another 4 h. The reaction mixture was concentrated and then purified by preparative LC (40-70% ACN in 0.1% TFA) to give the product as a yellow solid. The solid was dissolved in DCM/TFA (4:1, 5 mL) and the solution stirred at rt for 40 min to remove the boc protective group. The TFA salt of the product was recovered as a yellow solid of 93% purity. LCMS A: Rt 1.94/1.99, m/z [M+H]$^+$ 477.1, B: Rt 2.28.

(3E,5E)-1-(4-ethoxy-4-oxobutanoyl)-3,5-bis[(4-nitrophenyl)methylidene]-4-oxoazepan-1-ium trifluoroacetate (compound #1507). Intermediate 1 (35 mg, 0.09 mmol) and N-boc proline (22 mg, 0.10 mmol) were dissolved in DCM/DMF (4:1, 2 mL). TEA (19 µL, 0.14 mmol) was added and the mixture stirred for 5 min, then HATU (38.6 mg, 0.10 mmol) was added and the reaction stirred at rt overnight. More TEA (19 µL, 0.14 mmol) and HATU (38.6 mg, 0.10 mmol) were added and the reaction stirred for another 4 h. The reaction mixture was concentrated and then purified on preparative LC (40-70% ACN in 0.1% TFA) to give the TFA salt of the product as a yellow solid of 95% purity. LCMS A: Rt 2.48/2.50 m/z [M+H]$^+$ 508.1. B: Rt 2.48/2.52.

(3E,5E)-3,5-bis[(4-chlorophenyl)methylidene]azepan-4-one (compound #1518). Azepan-4-one hydrochloride (0.45 g, 3.0 mmol) and 4-chlorobenzaldehyde (0.92 g, 6.6 mmol) were dissolved in acetic acid (10 mL), conc. H$_2$SO$_4$ (1 mL) was added drop-wise and the reaction stirred at rt for 24 h. After addition of water (30 mL) a precipitate was formed, filtered off, and dried in vacuum to give the product in 91% purity as a yellow solid. LCMS A: Rt 2.04 m/z [M]$^+$ 358.1.

(3E,5E)-3,5-bis(phenylmethylidene)-1-(prop-2-enoyl) azepan-4-one (compound #1520). Azepan-4-one hydrochloride (50 mg, 0.182 mmol), acrylic acid (14 µL, 0.20 mmol), TBTU (58 mg, 0.182 mmol) and TEA (37 mg, 0.364 mmol) were dissolved in DMF (2 mL) and stirred at rt overnight. Brine and ethyl acetate were added and the phases separated. The organic phase was dried and the solvents evaporated after filtration. The crude product was dissolved in acetic acid (2 mL) and H$_2$SO$_4$ (0.2 mL). Benzaldehyde (50 µL) was added and the reaction stirred for 24 hours. Methanol and water were added to the mixture, which was purified by preparative LC. The title compound was isolated in 96% purity as a yellow solid. LCMS A: Rt 2.68 m/z [M+H]$^+$ 344.1.

(3E,5E)-3,5-bis(phenylmethylidene)-1-cyclobutanecarbonylazepan-4-one (compound #1521). Azepan-4-one hydrochloride (50 mg, 0.182 mmol), cyclobutyric acid (14 µL, 0.20 mmol), TBTU (58 mg, 0.182 mmol) and TEA (37 mg, 0.364 mmol) were dissolved in DMF (2 mL) and stirred at rt overnight. Brine and ethyl acetate were added and the phases separated. The organic phase was dried and the solvents evaporated after filtration. The crude product was dissolved in acetic acid (2 mL) and H$_2$SO$_4$ (0.2 mL). Benzaldehyde (50 was added and the reaction stirred for 24 h. Methanol and water were added to the mixture, which was purified by preparative LC. The title compound was isolated in 96% purity as a yellow solid. LCMS A: Rt 2.68 m/z [M+H]$^+$ 372.1.

(3E,5E)-1-(2-cyclopropylacetyl)-3,5-bis[(4-methoxyphenyl)methylidene]azepan-4-one (compound 1526). Azepan-4-one hydrochloride (0.45 g, 3.0 mmol) and 4-methoxybenzaldehyde (0.90 g, 6.6 mmol) were dissolved in acetic acid (10 mL), conc. H$_2$SO$_4$ (1 mL) was added drop-wise, and the reaction stirred at rt for 24 h. Water (30 mL) was added. The precipitate was filtered off and dried in vacuum over night. The crude material (30 mg, 0.107 mmol), cyclopropylacetic acid (12 mg, 0.12 mmol), TBTU (41 mg, 0.13 mmol) and TEA (26 mg, 0.26 mmol) were dissolved in DMF (2 mL) and stirred at rt over night. Methanol (1.5 mL) and water (0.5 mL) were added and the product was purified by preparative LC to yield the solid product in 95% purity. LCMS A: Rt 2.51 m/z [M+H]$^+$ 432.2.

(3E,5E)-5-[(3-nitrophenyl)methylidene]-3-(phenylmethylidene)azepan-4-one (compound #1560). N-boc-Azepan-4-one (0.10 g, 0.47 mmol) and 3-nitrobenzaldehyde (156 mg, 1.0 mmol) were dissolved in acetic acid (5 mL), concentrated H$_2$SO$_4$ (0.5 mL) was added drop-wise and the reaction stirred at rt for 4 days. Then more concentrated H$_2$SO$_4$ (0.5 mL) and aldehyde (156 mg, 1.0 mmol) were added and stirring continued at rt for three weeks. A mixture of the mono- and di-condensation products was obtained. The mixture was purified by column chromatography (DCM/methanol) to give the intermediate amine Intermediate 2 as a brown oil (19 mg). Intermediate 2 was dissolved in acetic acid (1.5 mL) together with benzaldehyde. Conc. H$_2$SO$_4$ (0.05 mL) was added and the reaction stirred at rt overnight. Then more H$_2$SO$_4$ was added and the stirring continued for a week. More aldehyde (156 mg, 1.0 mmol) and H$_2$SO$_4$ was added and stirring continued for an additional 4 days. The reaction mixture was concentrated and purified by preparative LC to give the TFA-salt of the product as yellow solid in 98% purity. LCMS System A: Rt 1.78 m/z [M+H]$^+$ 335.1, System B: Rt 2.43/2.28.

(3E,5E)-1-methyl-3,5-bis[(4-nitrophenyl)methylidene] azepan-4-one (compound #1563). N-methylazepan-4-one-.HCl (50 mg, 0.30 mmol) and 4-nitrobenzaldehyde were dissolved in acetic acid (5 mL) and stirred for 10 min, then conc. H$_2$SO$_4$ (50 µL) was added slowly and the mixture was stirred at rt overnight. More concentrated H$_2$SO$_4$ (100 µL) was added and stirring was continued at rt for 6 h. Additional 500 µL of concentrated H$_2$SO$_4$ was added and the reaction stirred overnight. A further 350 µL of conc. H$_2$SO$_4$ was added and stirring continued for additional 5 h, during which period further H$_2$SO$_4$ was added in two portions (500 µL and 250 µL). Then water (3x reaction volume) was added and the mixture was stirred until rt was reached. The reaction mixture was extracted with ethyl acetate (3x reaction volume). The phases were separated and the organic phase concentrated to yield a dark yellow viscous oil. The crude product was purified by preparative HPLC, (XBridge column; eluents 50 mM ammonium carbonate buffer at pH 10 and methanol) giving the title product as a yellow solid (26.3 mg). LCMS System A: Rt 1.87 m/z [M+H]$^+$ 394.1, System B: Rt 2.57.

(3E,5E)-3,5-bis[(4-fluorophenyl)methylidene]-1-propylazepan-4-one (compound #1574). Azepan-4-one hydrochloride (0.25 g, 1.68 mmol) and 4-fluorobenzaldehyde (0.416 g, 3.36 mmol) were dissolved in acetic acid (20 mL) and the solution stirred for 10 min, then conc. H$_2$SO$_4$ (200 µL) was slowly added and the solution was stirred at rt overnight. More conc. H$_2$SO$_4$ (1 mL) was added and stirring continued at rt. Another mL of conc. H$_2$SO$_4$ was added after 6 h, and the reaction stirred again overnight. The next day further 800 µl of conc. H$_2$SO$_4$ was added and stirring continued for a period of five days, during which two portions of H$_2$SO$_4$ (1 mL and 0.5 mL) were added to the reaction mixture. Then water (3x reaction volume) was added and the mixture stirred until rt was reached. The reaction mixture was extracted with ethyl acetate (10x reaction volume). The organic phase was concentrated by evaporation. Water was added to the residue. A precipitate was formed and filtered off. The solid was washed with water and dried in vacuum to give Intermediate 3 as a yellow solid. A portion (15 mg, 0.05 mmol) thereof was dissolved in DCE-Propanal (4 µL, 0.06 mmol) was added, and the mixture stirred for 15 min at rt. Then NaBH(OAc)$_3$ (15.7 mg, 0.07 mmol) and acetic acid (2.6 µL, 0.05 mmol) were added and the reaction stirred at rt over night. The reaction was concentrated and the crude product purified by preparative LC giving the product (7.2 mg) in 90% purity. LCMS System A: Rt 2.02 m/z [M+H]$^+$ 368.1, System B: Rt 3.21.

(3E,5E)-3-[(4-methoxyphenyl)methylidene]-5-[(4-nitrophenyl)methylidene]azepan-4-one (compound #1575). Azepan-4-one hydrochloride (0.25 g, 1.68 mmol) and 4-nitrobenzaldehyde (253 mg, 1.68 mmol) were dissolved in acetic acid (20 mL) and stirred for 10 min, then conc. H$_2$SO$_4$ (1 mL) was slowly added and the mixture stirred at rt for 8 days. On days 1-3 one portion conc. H$_2$SO$_4$ per day was added (0.5 mL, 0.75 mL, and 0.5 mL). Water (2× reaction volume) was added and the mixture extracted with ethyl acetate (2× reaction volume). The organic phase was concentrated by evaporation and dried to yield crude Intermediate 4. A portion of Intermediate 4 (100 mg, 0.41 mmol) was dissolved in acetic acid (6 mL) and stirred for 10 min, then concentrated H$_2$SO$_4$ (0.6 mL) was added slowly and the reaction stirred at rt for 6 days. Upon addition of water the product precipitated as a yellow solid. The precipitate was filtered off, washed with water and dried in vacuum to give the title compound as a yellow solid in 98% purity. LCMS System A: Rt 1.82 m/z [M+H]$^+$ 365.1, System B: Rt 2.41. $^1$H-NMR (400 MHz, CDCl$_3$) [ppm]=2.97-2.99 (m, 2H), 3.41-3.44 (m, 2H), 3.83 (bs, 3H), 4.28 (s, 2H), 7.06-7.08 (d, 2H), 7.47 (s, 1H), 7.59-7.62 (d, 2H), 7.76 (s, 1H), 7.78-7.80 (d, 2H), 8.27-8.29 (d, 2H).

(3E,5E)-5-[(4-fluorophenyl)methylidene]-3-[(4-methoxyphenyl)methylidene]-1-methylazepan-4-one (compound #1577). N-methylazepan-4-one hydrochloride (75 mg, 0.46 mmol) and 4-fluorobenzaldehyde were dissolved in acetic acid (7 mL) and stirred for 10 min, then conc. H$_2$SO$_4$ (350 µl) was added slowly and the mixture was stirred at rt for 8 days. More conc. H$_2$SO$_4$ was added during days 2-4 (0.175 mL, 0.35 mL, 0.25 mL respectively). Water was added and the solution extracted with ethyl acetate (twice the volume of reaction mixture). The organic phase was concentrated to give Intermediate 5. A portion of this intermediate (35 mg, 0.15 mmol) and 4-methoxybenzaldehyde (17 µL, 0.15 mmol) were dissolved in acetic acid (2.5 mL) and stirred for 10 min, then conc. H$_2$SO$_4$ (0.20 mL) was added slowly and the reaction stirred for five days. Water (2× reaction volume) was added and the reaction mixture extracted with ethyl acetate (2× reaction volume). The organic layer was concentrated and water was added. A precipitate was formed and filtered off to give the title product (11.2 mg) in 91% purity as a yellow solid. LCMS System A: Rt 1.86 m/z [M+H]$^+$ 352.1, System B: Rt 2.79.

(3E,5E)-1-acetyl-5-[(4-fluorophenyl)methylidene]-3-[(4-ethoxyphenyl)methylidene]azepan-4-one (compound #1579). Azepan-4-one hydrochloride (0.25 g, 1.68 mmol) and 4-fluorobenzaldehyde (179 µL, 1.68 mmol) were dissolved in acetic acid (20 mL) and stirred for 10 min, then conc. H$_2$SO$_4$ (1 mL) was slowly added and the mixture was stirred at rt for 8 days with addition of conc. H$_2$SO$_4$ during the first three days (0.5 mL, 0.75 mL and 0.5 mL respectively). Water (2× reaction volume) was added and the mixture extracted with ethyl acetate (2× mixture volume). The organic phase was concentrated and dried to give the crude Intermediate 6. A portion of this intermediate (100 mg, 0.46 mmol) was dissolved in acetic acid (6 mL) and stirred for 10 min, then concentrated H$_2$SO$_4$ (0.6 mL) was added slowly and the reaction stirred at rt for 7 days. Water was added (1× volume) and the mixture was neutralized with saturated aqueous NaHCO$_3$. The formed precipitate was filtered off, washed with water and dried in vacuum to yield Intermediate 7 (31.5 mg) as a yellow solid of 91% purity. LCMS System A: Rt 1.85 m/z [M+H]$^+$ 338. Intermediate 7 (10 mg) was dissolved in DCM (1 mL) and TEA (5.0 µL, 0.04 mmol) was added. The mixture was stirred for 10 min, then acetyl chloride (2.3 µL, 0.03 mmol) was added and the reaction stirred at rt for 30 min. The reaction was washed with water, saturated aqueous NaHCO$_3$ and brine. The organic phase was concentrated to give the title compound (6.4 mg) as a yellow solid of 90% purity. LCMS System A: Rt 2.35 m/z [M+H]$^+$ 380.1, System B: Rt 2.37. $^1$H-NMR (400 MHz, CDCl$_3$): [ppm]=1.70, 1.90, 1.98 and 1.99 (4×s, 3H, CH$_3$CO—, signals from the two regioisomers and their acetate rotamers), 2.89-3.01 (m, 2H), 3.68-3.77 (m, 2H), 3.79, 3.79, 3.79, 3.08 (4×s, 3H, —OMe, signals from the two regioisomers and their acetate rotamers), 4.65-4.68 (m, 2H), 7.0-7.04 and 7.098-7.103 (2×m, 2H), 7.22-7.30 (m, 3H), 7.48-7.62 (m, 5H).

(3E,5E)-5-[(4-chlorophenyl)methylidene]-3-[(4-nitrophenyl)methylidene]azepan-4-one (compound #1583). N-methylazepan-4-one hydrochloride (75 mg, 0.46 mmol) and 4-chlorobenzaldehyde (64 mg, 0.46 mmol) were dissolved in acetic acid (7 mL) and stirred for 10 min, then conc. H$_2$SO$_4$ (350 µl) was added slowly and the mixture was stirred at rt for 8 days. More conc. H$_2$SO$_4$ was added during days 2-4 (0.175 mL, 0.35 mL, 0.25 mL respectively). Water (2× reaction volume) was added and the solution extracted with ethyl acetate (2× reaction volume). The organic phase was concentrated to give Intermediate 8. A portion of the intermediate (35 mg, 0.14 mmol) and 4-nitrobenzaldehyde (69.5 mg, 0.46 mmol) were dissolved in acetic acid (2.5 mL) and stirred for 10 min, then conc. H$_2$SO$_4$ (200 µL) was added slowly and the mixture was stirred at rt for 5 days. More conc. H$_2$SO$_4$ (0.2 mL) was added, and stirring continued for 5 more days. Water (2× reaction volume) was added and the solution extracted with ethyl acetate (2× reaction volume). The organic phase was concentrated and the residue purified by preparative LC to give the title compound (1.8 mg) as a yellow solid of 94% purity. LCMS System A: Rt 1.98/2.04 m/z [M+H]$^+$ 383.1, System B: Rt 2.82/2.98.

ABBREVIATIONS

Boc tert-butyloxycarbonyl
ACN acetonitrile
DCM dichloromethane
TFA trifluoroacetic acid
DMF dimethylformamide
TEA triethylamine
Rt retention time
TBTU O-(benzotriazol-1-yl)-N,N,N',N'-tetramethyluronium tetrafluoroborate)
rt room temperature
LC liquid chromatography
EDC 1-Ethyl-3[3-dimethylaminopropyl]carbodiimide
HATU 2-(1H-7-Azabenzotriazol-1-yl)-1,1,3,3-tetramethyl uronium hexafluorophosphate;
DCE 1,2-Dichloroethane

EXAMPLE 3

Pharmaceutical composition A (aqueous suspension). The compound of the invention (25 mg) is dissolved in 1 ml of dimethyl sulfoxide. The solution is added drop-wise to 10 ml of vigorously stirred saline. The formed suspension, which can be stabilized by adding 1% by weight of PVP, can be used for intramuscular, intravenous or subcutaneous administration.

EXAMPLE 4

Pharmaceutical composition B (tablet). Tablets for oral administration are produced by blending 2.0 g of the compound of the invention (powder, <10 mµ, 90%) with microcrystalline cellulose (1.30 g), corn starch (0.50) g, silica (0.20) g, Mg stearate (0.12 mg). The mixture is dry compressed to 400 mg tablets, which are sugar coated.

EXAMPLE 5

Pharmaceutical composition C (solution). The compound of the invention (10 mg) is dissolved in 0.5 ml of Cremophor EL (BASF Corp.) and absolute ethanol was added to 1.0 ml. The clear solution is filled into glass vials for injection.

EXAMPLE 6

Pharmaceutical composition D (solution). For intraperitoneal administration in animal studies an aqueous composition a stock solution was prepared by dissolving the compound of the invention to a concentration of 2 mg/ml in Chremaphor EL/polyethylene glycol 400 1:1. (v/v) at room temperature or by heating to up to about 80° C. assisted by ultrasonication. A aliquot of the stock solution was diluted 1:10 with 0.9% saline and used immediately for IP injection.

EXAMPLE 7

Pharmaceutical composition E (solution). For intraperitoneal administration a 25% by weight Kolliphor HS15 stock solution was prepared by melting an entire container of Kolliphor HS15 (Sigma 42966) by warming to 60° C. and diluting with deionized water to 25% w/w. To compound #1570 (18.0 mg) in a 10 mL sample tube was added 10.0 mL of the stock solution and the tube vortexed, treated with ultrasound at about 50° C. for about 2 h, and occasionally heated to about 83° C. The clear solution obtained was sterile filtered through a 0.2 µm cellulose syringe filter prior to injection. By the same procedure solutions of compounds #1546 and #1571 were prepared; these compounds were however not fully dissolved. The non-dissolved residue was weighed, and the weight deducted from the starting weight of compound (18 mg). It was found that the prepared solutions (10 ml) contained 8.5 mg and 11.0 mg, respectively, of compounds #1546 and #1571.

EXAMPLE 8

Pharmaceutical composition F (solution). For intraperitoneal administration a stock solution of 2-hydroxypropyl-β-cyclodextrin (Aldrich 332593) was prepared by dissolving the cyclodextrin in deionized water to a concentration of 30% w/w. To compound #1649 (15.0 mg) in a 10 mL sample tube was added 10.0 mL of the stock solution. The tube was vortexed, treated with ultrasound at about 50° C. for about 2 h, and occasionally heated to about 83° C. The solution obtained was sterile filtered through a 0.2 µm cellulose syringe filter prior to injection. The weight of residual compound #1659 not dissolved was determined and used for correcting the concentration of the filtered solution to 82.5% of the attempted concentration. By the same procedure a solution of compound #1546 was prepared.

EXAMPLE 9

The compound of the invention induces proteasome inhibition. The reporter cell line MelJuSo Ub-YFP, which is engineered to accumulate yellow fluorescent protein (YFP) upon proteasome inhibition (12), was used for compound evaluation. The accumulation of YFP was measured for 48 hours in an IncuCyte-FLR system (Essen Bioscience, Essen, UK), which is an automated fluorescence microscope. Numbers of positive cells per field were used as a measure of proteasome inhibition.

EXAMPLE 10

Determination of solubility of compounds of the invention in aqueous media. In the diagrams of FIGS. 2a-2e solubility is expressed as Log S (mmol/ml; software ACD/Labs Inc.) Solubility is determined in aqueous buffer at various pH values and predicted for pure water at 25° C. The algorithm uses a set of >6,800 compounds as reference. The diagrams show that azepanones of the invention can have a substantially increased solubility, such as by a factor 2 or more, in aqueous media at physiological pH, such as at a pH from 6 to 8, in particular of from 7.0 to 7.5, in comparison with correspondingly substituted piperidin-4-ones.

EXAMPLE 11

Figure 3A:
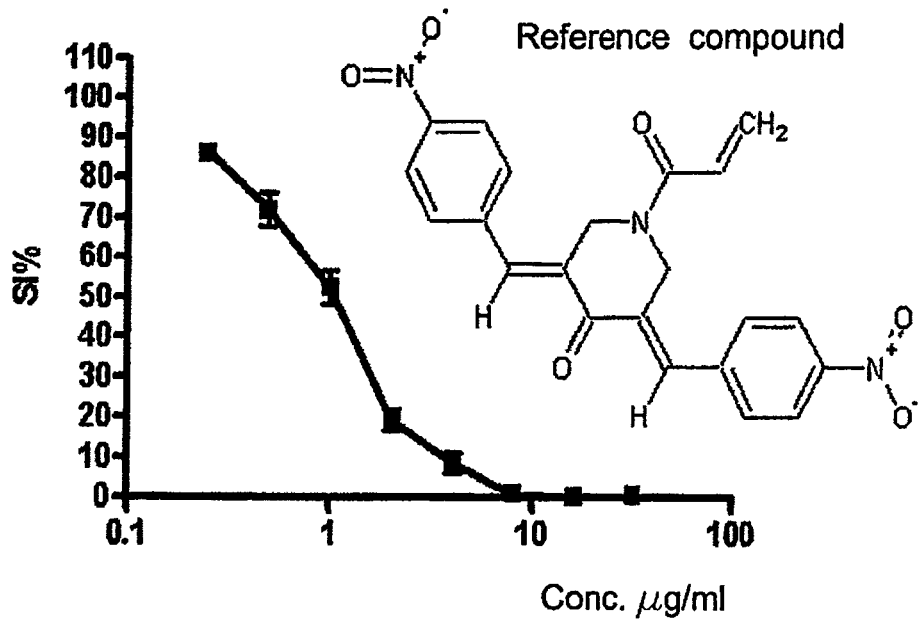
FIGS. 3a to 3f are diagrams illustrating, by the method of FIGS. 1a to 1o, the superior cytotoxicity of azepanone compounds of the invention in relation to structurally corresponding piperidin-4-one compounds not comprised by the invention.
Figure 3B:
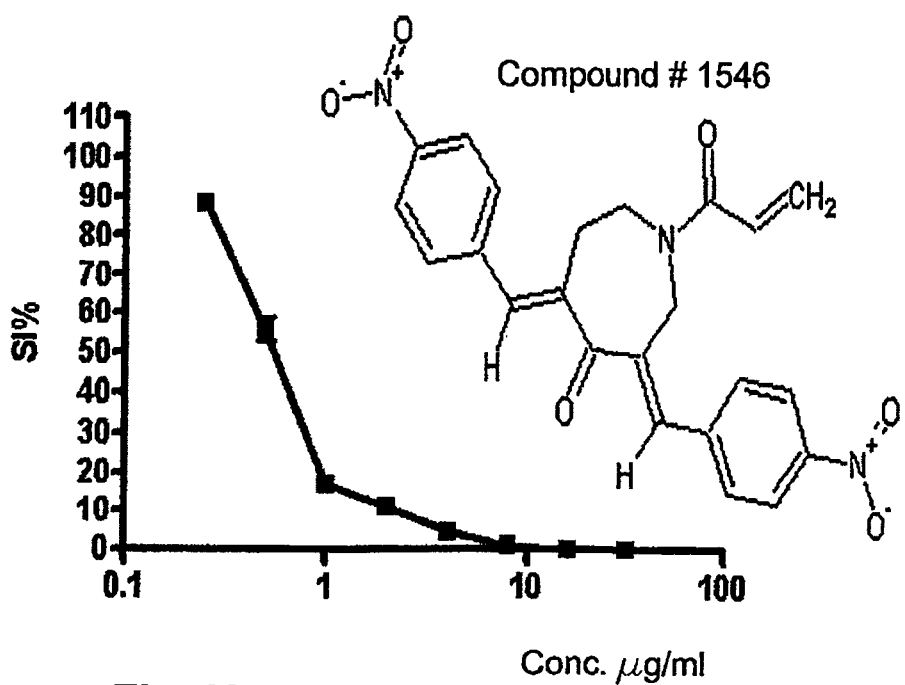
Figure 3C:
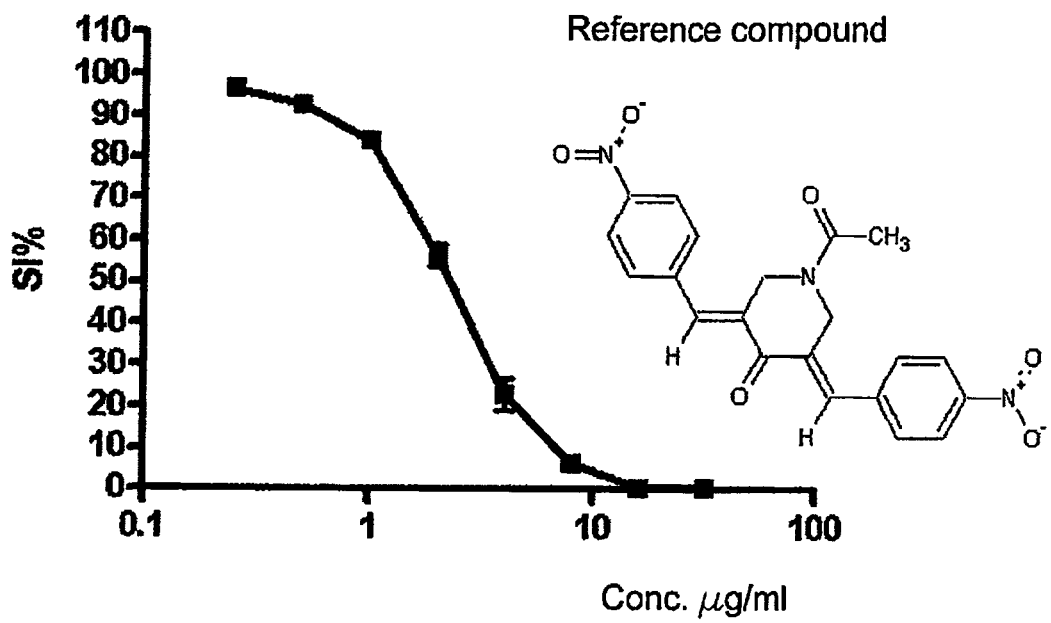
Figure 3D:
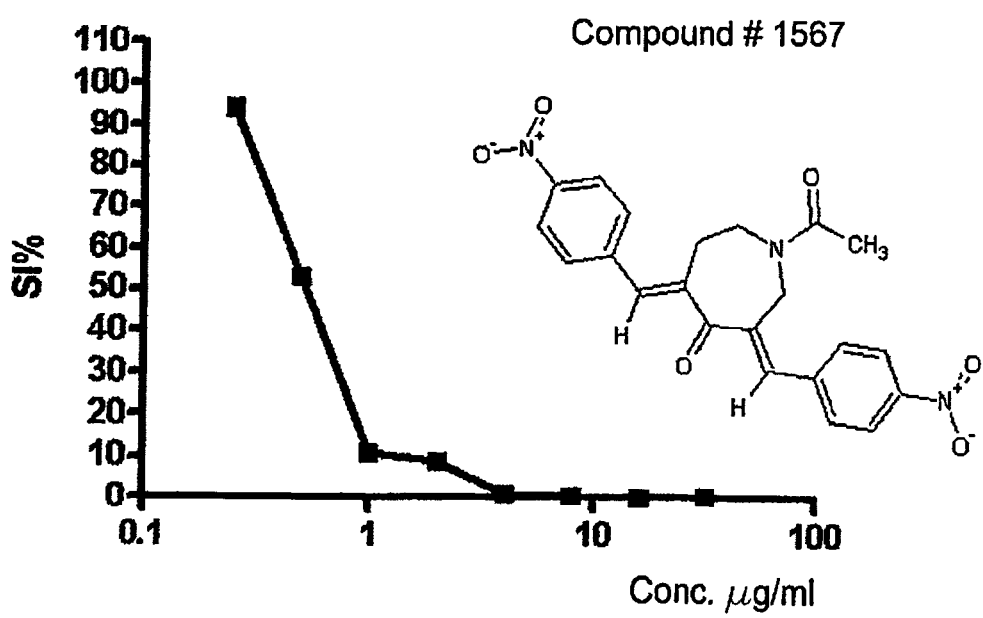
Figure 3E:
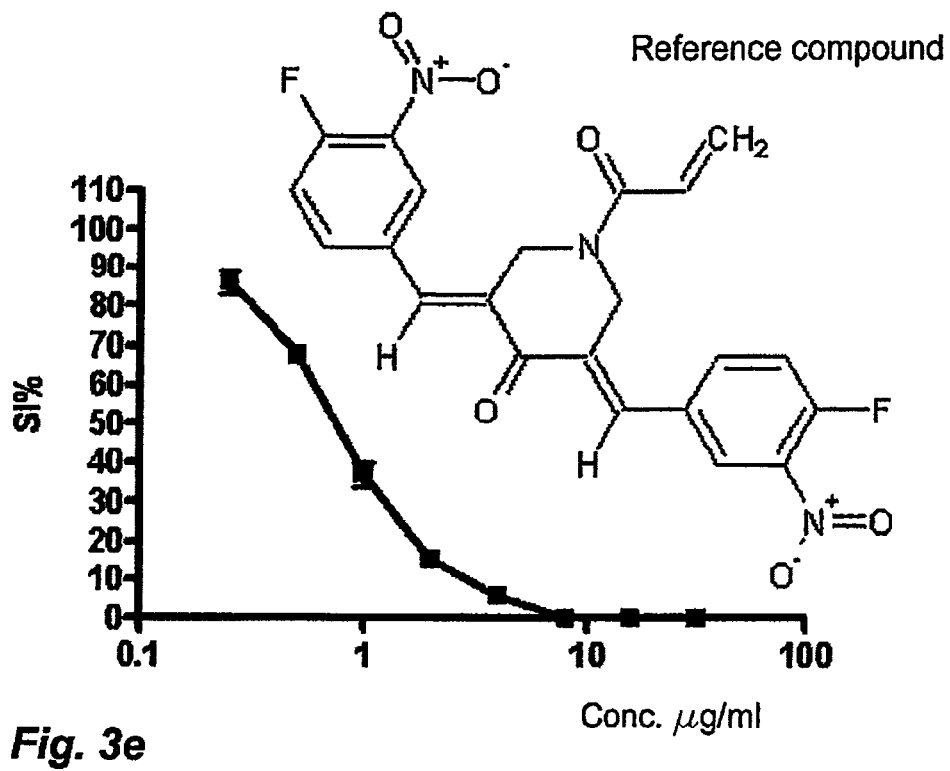
Figure 3F:
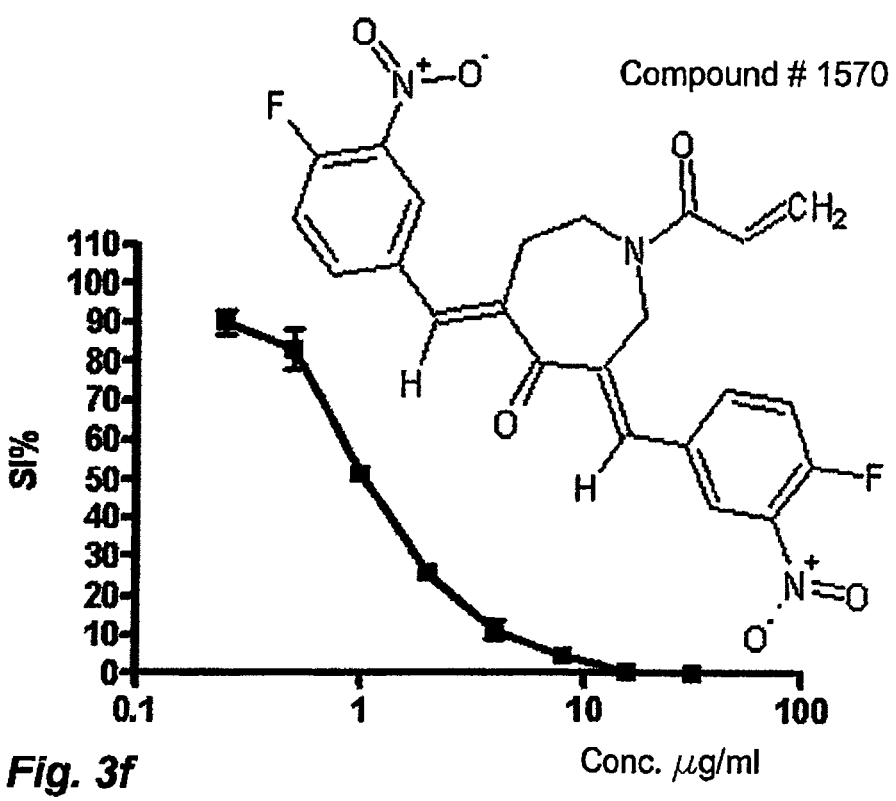

Azepanes/Azepanones of the Invention Exhibit Higher Cytotoxicity than Structurally Corresponding piperidines/piperidin-4-ones FIGS. 3b, 3d, 3f are diagrams illustrating the cytotoxicity of compounds of the invention nos. 1546, 1547, and 1570 with a 7-membered ring moiety in comparison to structurally corresponding compounds not comprised by the invention with a 6-membered ring moiety. Their induction of dose-dependent cytotoxicity was determined after 72 hours of continuous compound exposure to the reporter cell line HCT-116. Treated cells were compared with untreated controls. Cytotoxicity is visualized as survival index (SI) over the range of about 90% SI to about 0% SI in dependence on compound concentration. It appears from the Figures that the compounds of the invention are more cytotoxic that the reference compounds since they are producing the same level of cytotoxicity at lower concentration.

References

1. Masdehors, P et al., *Increased sensitivity of CLL-derived lymphocytes to apoptotic death activation by the proteasome-specific inhibitor lactacystin*. Br J Haematol 105, 752-757, doi:bjh1388 [pii] (1999).
2. DeMartino, G N et al., *PA700, an ATP-dependent activator of the 20 S proteasome, is an ATPase containing multiple members of a nucleotide binding protein family*. J Biol Chem 69, 20878-20884, http://www.ncbi.nlm.nih.gov/entrez/query.fcgi?cmd=Retrieve&db=PubMed&dopt=Citation&list_uids=8063704 (1994) (1994).
3. Rechsteiner, M et al., *The multicatalytic and 26 S proteases*. J Biol Chem 268, 6065-6068, http://www.ncbi.nlm.nih.gov/entrez/query.fcgi?cmd=Retrieve&db=PubMed&dopt=Citation&list_uids=8454582 (1993).

4. Adams, J & Kauffman, M, *Development of the proteasome inhibitor Velcade (Bortezomib)*. Cancer Invest 22, 304-311, http://www.ncbi.nlm.nih.gov/entrez/query.fcgi?cmd=Retrieve&db=PubMed&dopt=Citation&list_uids=15199612 (2004).

5. Erdal, H et al., *Induction of lysosomal membrane permeabilization by compounds that activate p53-independent apoptosis*. Proc Natl Acad Sci USA 102, 192-197, doi:0408592102 [pii]10.1073/pnas.0408592102 (2005).

6. Berndtsson, M et al., *Induction of the lysosomal apoptosis pathway by inhibitors of the ubiquitin-proteasome system*. Int J Cancer 124, 1463-1469, doi:10.1002/ijc.24004 (2009).

7. Lamb, J et al., *The Connectivity Map: using gene-expression signatures to connect small molecules, genes, and disease*. Science 313, 1929-1935, doi:313/5795/1929 [pii] 10.1126/science.1132939 (2006).

8. Adams, J et al., *Potent and selective inhibitors of the proteasome: dipeptidyl boronic acids*. Bioorg Med Chem Lett 8, 333-338 333-338, doi:S0960894X98000298 [pH] (1998).

9. Shibata, T et al., *An endogenous electrophile that modulates the regulatory mechanism of protein turnover: inhibitory effects of 15-deoxy-Delta 12,14-prostaglandin J2 on proteasome*. Biochemistry 42, 13960-13968, doi:10.1021/bi035215a (2003).

10. Yang, H et al., *Celastrol, a triterpene extracted from the Chinese "Thunder of God Vine," is a potent proteasome inhibitor and suppresses human prostate cancer growth in nude mice*. Cancer Res 66, 4758-4765 4758-4765, doi:66/9/4758 [pii]10.1158/0008-5472.CAN05-4529 (2006).

11. Yang, H et al., *The tumor proteasome is a primary target for the natural anticancer compound Withaferin A isolated from "Indian winter cherry"*. Mol Pharmacol 71, 426-437, doi:mol.106.030015 [pii]10.1124/mol.106.030015 (2007).

12. Menendez-Benito, V et al., *Endoplasmic reticulum stress compromises the ubiquitin-proteasome system*. Hum Mol Genet 14, 2787-2799, doi:ddi312 [pii]10.1093/hmeddi312 (2005).

13. Mullally, J E & Fitzpatrick, F A, *Pharmacophore model for novel inhibitors of ubiquitin isopeptidases that induce p53-independent cell death*. Mol Pharmacol 62, http://www.ncbi.nlm.nih.gov/entrez/query.fcgi?cmd=Retrieve&db=PubMed&dopt=Citation&list_uids=12130688 (2002).

14. Guterman, A & Glickman, M H, *Complementary roles for Rpn11 and Ubp6 in deubiquitination and proteolysis by the proteasome*. J Biol Chem 279, 17291738, doi:10.1074/jbc.M307050200 [pii] (2004).

15. Hofmann, R M & Pickart, C M et al., *Noncanonical MMS2-encoded ubiquitin conjugating enzyme functions in assembly of novel polyubiquitin chains for DNA repair*. Cell 96, 645-653, doi:S0092-8674(00)80575-9 [pii] (1999).

16. Vong, Q P et al., *Chromosome alignment and segregation regulated by ubiquitination of surviving cells*. Science 310, 1499-1504, doi:310/5753/1499 [pii]10.1126/science.1120160 (2005).

17. Borodovsky, A et al., *A novel active site-directed probe specific for deubiquitylating enzymes reveals proteasome association of USP14*. EMBO J 20, 5187-5196, doi:10.1093/emboj/20.18.5187 (2001).

18. Lam, Y A et al., *Specificity of the ubiquitin isopeptidase in the PA700 regulatory complex of 26 S proteasomes*. J Biol Chem 272, 28438-28446, http://www.ncbi.nlm.nih.gov/entrez/query.fcgi?cmd=Retrieve&db=PubMed&dopt=Citation&list_uids=9353303 (1997).

19. Verma, R et al., *Role of Rpn11 metalloprotease in deubiquitination and degradation by the 26S proteasome*. Science 298, 611-615, doi:10.1126/science.10758981075898 [pii] (2002).

20. Yao, T & Cohen, R E, *A cryptic protease couples deubiquitination and degradation by the proteasome*. Nature 419, 403-407, doi:10.1038/nature01071nature01071 [pii] (2002).

21. Kramer, G et al., *Differentiation between cell death modes using measurements of different soluble forms of extracellular cytokeratin 18*. Cancer Res 64, 1751-1756 (2004) http://www.ncbi.nlm.nih.gov/entrez/query.fcgi?cmd=Retrieve&db=PubMed&dopt=Citation&list_uids=14996736 (2004).

22. Olofsson, M H et al., *Specific demonstration of drug-induced tumour cell apoptosis in human xenograft models using a plasma biomarker*. Cancer Biomarkers 5, 117-125, http://www.ncbi.nlm.nih.gov/pubmed/19407366 (2009).

23. Reyes-Turcu, F E et al., *Regulation and cellular roles of ubiquitin-specific deubiquitinating enzymes*. Annu Rev Biochem 78, 363-397, http://www.ncbi.nlm.nih.gov/entrez/query.fcgi?cmd=Retrieve&db=PubMed&opt=Citation&list_uids=19489724 (2009).

24. Koulich, E et al., *Relative structural and functional roles of multiple deubiquitylating proteins associated with mammalian 26S proteasome*. Mol Biol Cell 19, 1072-1082, doi:E07-10-1040 [pii]10.1091/mbc.E07-10-1040 (2008).

25. Bunz, F. et al., *Requirement for p53 and p21 to sustain G2 arrest after DNA damage*. Science 282, 1497-1501 (1998).

26. Pietenpol, J A et al., *Paradoxical inhibition of solid tumor cell growth by bcl2*. Cancer Res 54, 3714-3717 (1994).

27. Bodnar, A G et al., *Extension of life-span by introduction of telomerase into normal human cells*. Science 279, 349-352 (1998).

28. Lamb, J et al., *The Connectivity Map: using gene-expression signatures to connect small molecules, genes, and disease*. Science 313, 1929-1935, doi:313/5795/1929 [pii] 10.1126/science.1132939 (2006).

29. Elsasser, S et al., *Characterization of the proteasome using native gel electrophoresis*. Methods Enzymol 398, 353-363, doi:S0076-6879(05)98029-4 [pii]10.1016/S0076-6879(05)98029-4 (2005).

30. Guterman, A & Glickman, M H, *Complementary roles for Rpn11 and Ubp6 in deubiquitination and proteolysis by the proteasome*. J Biol Chem 279, 1729-1738, doi:10.1074/jbc.M307050200M307050200 [pH] (2004).

31. Hagg, M et al., *A novel high-through-put assay for screening of pro-apoptotic drugs*. Invest New Drugs 20, 253-259 (2002).

32. Lindhagen, E et al., *The fluorometric microculture cytotoxicity assay*. Nat Protoc 3, 1364-1369, doi: nprot.2008.114 [pii]10.1038/nprot.2008.114 (2008).

The invention claimed is:

1. A compound of the general structure S-1 capable of abrogating the deubiquitinating (DUB) activity of the 19S RP DUBs

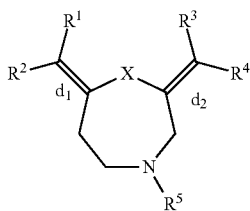

wherein
- R¹, R² at double bond d1 and R³, R⁴ at double bond d2 can, independent of each other, have a configuration opposite to that of formula S1,
- X is CO, CS, $CH_2$, $CHC_{1-6}$-alkyl, NH or $NC_{1-6}$-alkyl;
- R¹ and R³ are, independent of each other, H or $C_{1-6}$-alkyl;
- R² and R⁴ are, independent of each other, H; $C_{1-6}$-alkyl; $C_{1-5}$-alkyl-CO; phenyl or 6-membered heteroaryl optionally substituted by 1-3 of: $C_{1-6}$-alkyl, $C_{1-6}$-alkoxy, CN, —$COOC_{1-6}$-alkyl, COOH, $NO_2$, F, Cl, Br, I, $CF_3$, $NH_2$, $NHC_{1-6}$-alkyl, $N(C_{1-6}$-alkyl$)_2$, $CONR^7R^8$, with the proviso that one or more of H in alkyl and alkoxy can be substituted by fluoro;
- R⁵ is any of H; $C_{1-6}$-alkyl; $C_{2-6}$-alkenyl; $C_{1-3}$-alkoxy-$C_{1-6}$-alkyl-; $C_{1-3}$-alkoxy-$C_{2-6}$-alkenyl-; aryl-$C_{0-6}$-alkyl-; heteroaryl-$C_{0-6}$-alkyl-; heterocyclyl-$C_{0-6}$-alkyl-; cycloalkyl-$C_{0-6}$-alkyl-; $C_{1-6}$-alkyl-$COOC_{1-6}$-alkyl; -$C_{2-6}$-alkyl-aryloxy; $C_{1-6}$-alkyl-heteroaryl; $C_{1-6}$-alkyl-heterocyclyl; $C_{1-6}$-alkyl-cycloalkyl; $C_{1-6}$-alkyl-aryl; COR⁶;
- R⁶ is any of $C_{1-6}$-alkyl; $C_{2-6}$-alkenyl; $C_{1-6}$-alkoxy; $C_{1-3}$-alkoxy-$C_{1-6}$-alkyl-; $C_{1-3}$-alkoxy-$C_{2-6}$-alkenyl-; aryl-$C_{0-6}$-alkyl-; heteroaryl-$C_{0-6}$-alkyl-; heterocyclyl-$C_{0-6}$-alkyl-; cycloalkyl-$C_{0-6}$-alkyl-; -$C_{1-6}$-alkyl-$COOC_{1-6}$-alkyl; $NH_2$; —$NHC_{1-6}$-alkyl; —$N(C_{1-6}$-alkyl$)_2$; —$C_{0-6}$-alkyl-aryloxy; and
- R⁷, R⁸ are, independent of each other, H or $C_{1-3}$-alkyl.

2. The compound of claim 1 wherein X is CO.

3. The compound of claim 2, wherein R¹ and R³ are both H.

4. The compound of claim 1, wherein R² and R⁴ are, independent of each other, phenyl or 6-membered heteroaryl, optionally substituted by 1-3 of: $C_{1-6}$-alkyl, $C_{1-6}$-alkoxy, CN, —$COOC_{1-6}$-alkyl, COOH, $NO_2$, F, Cl, Br, I, $CF_3$, $NH_2$, $NHC_{1-6}$-alkyl, $N(C_{1-6}$-alkyl$)_2$, and $CONR^7R^8$.

5. The compound of claim 4, wherein R² and R⁴ are independently substituted phenyl in which substitution of the phenyl is in one or more of positions 3, 4, 5.

6. The compound of claim 1, wherein R¹, R² at double bond d1 and R³, R⁴ at double bond d2 have the configuration of formula S-1,
- X is CO, CS, $CH_2$, $CHC_{1-6}$-alkyl, NH or $NC_{1-6}$-alkyl;
- R¹ and R³ are, independent of each other, H or $C_{1-6}$-alkyl;
- R² and R⁴ are, independent of each other, H; $C_{1-6}$-alkyl; $C_{1-5}$-alkylCO; phenyl or 6-membered heteroaryl substituted with 1-3 of: CN, $NO_2$, F, Cl, Br, I, $NH_2$, $NHC_{1-6}$-alkyl, $N(C_{1-6}$-alkyl$)_2$, $COOC_{1-6}$-alkyl; and
- R⁵ is H, $C_{1-6}$-alkyl, $C_{2-6}$-alkenyl, $C_{1-3}$-alkoxy-$C_{1-6}$-alkyl, $C_{1-3}$-alkoxy-$C_{2-6}$-alkenyl, aryl, heteroaryl, heterocyclyl, $C_{1-6}$-alkyl-heteroaryl, $C_{1-6}$-alkyl-heterocyclyl, $C_{1-6}$-alkyl-cycloalkyl, $C_{1-6}$-alkyl-aryl, CO—$C_{1-6}$-alkyl, CO-vinyl, CO-allyl, CO-aryl, CO-cycloalkyl.

7. The compound of claim 6, wherein X is CO.

8. The compound of claim 6, wherein R² and R⁴ are substituted phenyl.

9. The compound of claim 6, wherein R⁵ is selected from CO—$C_{1-6}$-alkyl, CO-cycloalkyl, CO-vinyl, and CO-allyl.

10. A method of treating a cancer in a person, wherein the cancer is selected from the group consisting of colon cancer tumor, multiple myeloma tumor, FaDu tumor, lung cancer tumor, breast cancer tumor and acute myeloid leukemia, comprising administering to the person, in a pharmaceutically acceptable carrier, a pharmacologically effective dose of the compound of claim 1.

11. The method of claim 10, wherein the compound is dissolved or suspended in a liquid carrier.

12. The method of claim 10, wherein administration is by intravenous, intramuscular, intraperitoneal or subcutaneous injection or infusion.

13. The method of claim 10, wherein administration is peroral.

14. The method of claim 13, wherein the carrier is a tablet or capsule.

15. The method of claim 10, wherein the pharmacologically effective dose is from 0.0001 g/kg to 0.1 g/kg body weight.

16. The method of claim 10, wherein the pharmacologically effective dose is from 0.001 g/kg to 0.01 g/kg body weight.

17. The method of claim 10, comprising selecting a person to be treated by determining the growth rate of a tumor of the cancer prior to and upon administration of bortezomib or an agent sharing the apoptosis generating activity of bortezomib or other anti-cancer drug, wherein a positive growth rate constitutes a selection marker.

18. A pharmaceutical composition comprising the compound of claim 1 and a pharmaceutically acceptable carrier.

19. The composition of claim 18, in the form of a tablet or capsule or other single-dose preparation for peroral administration.

20. The composition of claim 18, in the form of a solution or suspension in a pharmaceutically acceptable liquid carrier adapted for injection or infusion.

21. The composition of claim 18, adapted for intravenous, intramuscular, intraperitoeal or subcutaneous infusion or injection.

22. The compound of claim 1, wherein X is CO, R¹ and R³ are both H, R² and R⁴ are both 4-flouro-3-nitrophenyl, R⁵ is COR⁶, and R⁶ is vinyl.

23. The compound of claim 1, wherein X is CO, R¹ and R³ are both H, R² and R⁴ are both 4-fluoro-3-nitrophenyl, R⁵ is COR⁶, and R⁶ is methyl.

24. A pharmaceutical composition comprising the compound of claim 22 and a pharmaceutically acceptable carrier.

25. A pharmaceutical composition comprising the compound of claim 23 and a pharmaceutically acceptable carrier.

26. The method of claim 10, wherein X is CO, R¹ and R³ are both H, R² and R⁴ are both 4-fluoro-3-nitrophenyl, R⁵ is COR⁶, and R⁶ is vinyl.

27. The method of claim 10, wherein X is CO, R¹ and R³ are both H, R² and R⁴ are both 4-fluoro-3-nitrophenyl, R⁵ is COR⁶, and R⁶ is methyl.

28. A method of abrogating the DUB activity of 19S RP DUBs comprising UCHL5 and USP14 in tumor cells in a person who has tumor cells having such DUB activity, comprising administering to the person, in a pharmaceutically acceptable carrier, a pharmacologically effective dose of the compound of claim 1.

29. The method of claim 28, wherein the deubiquitinating (DUB) activity of non-proteasomal DUBs is not affected.

30. The method of claim 28, wherein X is CO, $R^1$ and $R^3$ are both H, $R^2$ and $R^4$ are both 4-flouro-3-nitrophenyl, $R^5$ is $COR^6$, and $R^6$ is vinyl or methyl.

* * * * *